Figure 1:
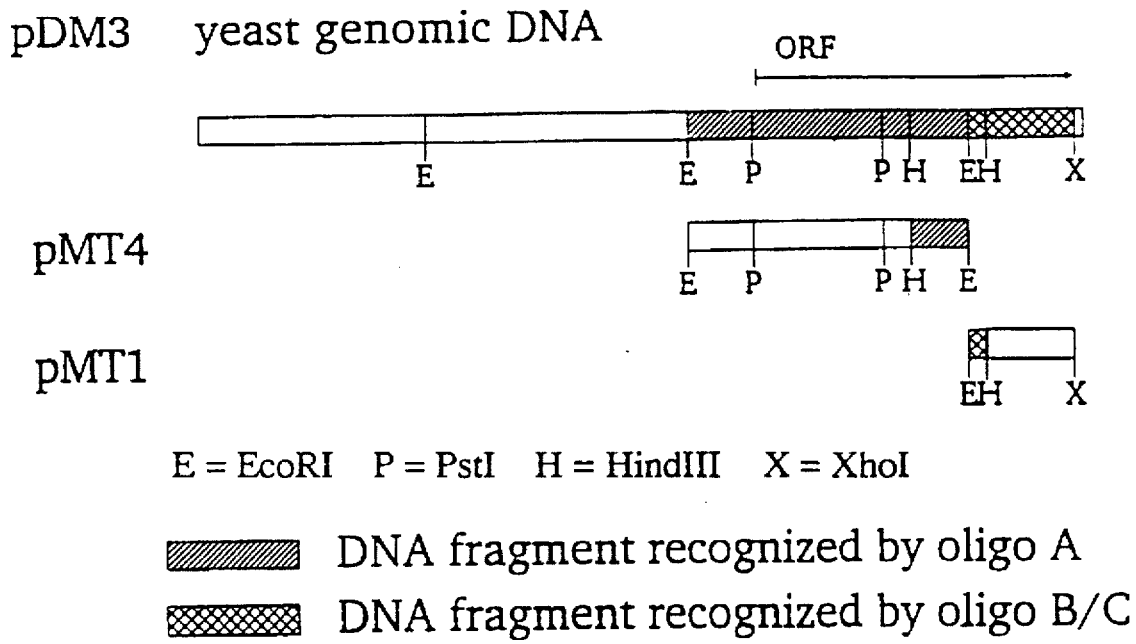

US005714377A

United States Patent [19]
Tanner et al.

[11] Patent Number: 5,714,377
[45] Date of Patent: Feb. 3, 1998

[54] MODIFIED FUNGAL CELLS AND METHOD FOR PRODUCING RECOMBINANT PRODUCTS

[75] Inventors: Widmar Tanner; Sabine Strahl-Bolsinger, both of Regensburg, Germany; Reinhard Fleer, Bures sur Yvette; Alain Fournier, Chatenay Malabry, both of France

[73] Assignee: Rhone-Poulenc Rorer S.A., Antony Cedex, France

[21] Appl. No.: 381,931

[22] PCT Filed: Aug. 16, 1993

[86] PCT No.: PCT/EP93/02179

§ 371 Date: Apr. 18, 1995

§ 102(e) Date: Apr. 18, 1995

[87] PCT Pub. No.: WO94/04687

PCT Pub. Date: Mar. 3, 1994

[30] Foreign Application Priority Data

Aug. 14, 1992 [DE] Germany .................. 42 26 971.7

[51] Int. Cl.$^6$ .................. C12N 1/15; C12N 1/16; C12P 21/02; C07H 21/04
[52] U.S. Cl. .................. 435/254.11; 435/69.1; 435/254.2; 435/254.21; 536/23.2
[58] Field of Search .................. 435/254.11, 69.1, 435/254.2, 254.21; 536/23.2

[56] References Cited

FOREIGN PATENT DOCUMENTS

| 0 001 929 | 6/1979 | European Pat. Off. . |
| 0 241 435 | 10/1987 | European Pat. Off. . |
| 0 361 991 | 4/1990 | European Pat. Off. . |
| 0 433 117 | 6/1991 | European Pat. Off. . |

OTHER PUBLICATIONS

Bimbaum, et al., "A rapid alkaline axtraction procedure for screening recombinant plasma DNA", *Nuc.Acids Res.* 7:1513 (1979).
Broach, "The Yeast Plasmid 2μ Circle", *Cell*, 28:203–204, (1982).
de Louvencourt, et al., "Transformation of *Kluyveromyces lactis* by Killer Plasmid DNA", *J.Bacteriol.* 154:737–742 (1983).
Domdey,et al., "Lariat Structures Are In Vivo Intermediates in Yeast Pre–mRNA Splicing", *Cell*:39, 611–621 (1984).
Durrens, et al, "Expression of the avian gag–myc oncogene in *Saccharomyces cerevisiae*", *Cur. Genet.* 18:7–12 (1990).
Emr, et al., "An MFα1–SuC2 (α–factor–invertase) gene fusion for study of protein localization and gene expression in yeast", *Proc.Natl.Acad.Sci. (USA)* 80:7080–7084, (1983).
Ernst, et al., "O–Glycosylation and novel processing events during secretion of α–factor/GM–CSF Fusions by *Saccharomyces cerevisiae*", *Bio–Technology* 5:831–834 (1987).
Feizi and Childs, "Carbohydrates as antigenic determinants of glycoproteins", *Biochem*, 245:1–11 (1987).

Fleer, "Engineering yeast for high level expression", *Curr. Opin.Biotechnol.* 3:486–496 (1992).
Grunstein and Hogness, "Colony hybridization: A method for the isolation of cloned DNAs that contain a specific gene", *Proc.Nat.Acad.Sci. (USA)* 72:3961–3965 (1975).
Guthrie and Abelson "Organization and Expression of tRNA Genes in *Saccharomyces cerevisiae*", in *the Moleculat Biology of Yeast Saccharomyces*, Strathern, et al., (eds) pp. 487–528 (1982).
Hanahan, "Studies on Transformation of *Escherichia coli* with Plasmids", *J.Miol.Biol.* 166:557–580 (1983).
Hård, et al., "O–mannosylation of recombinant human insulin–like growth factor I(IGF–1) Produced in *Saccharomyces cerevisiae*", *FEBS Letters* 248:111–114 (1989).
Henikoff, "Undirectional Digestion with Exonuclease III in DNA Sequence Analysis", *Meth.Enzymol.* 155:156–165 (1987).
Hoffman and Winston, "A ten–minute DNA preparation from yeast efficiently releases autonomous plasmids for transformation of *Escherichia coli*", *Gene*: 57:267–272 (1987).
Iot, et al., "Transformation of Intact Yeast Cells Treated with Alkali Cations", *J.Bacteriol.* 153:163–168 (1983).
Julius, et al., "Isolation of the Putative Structural Gene for the Lysine–Arginine–Cleaving Endopeptidase Required for Processing of Yeast Prepo–α–Factor", *Cell* 37:1075–1089 (1984).
Karube, et al., "Transfusion of *Saccharomyces cerevisiae* spheroplasts by high electric pulse", *FEBS Letters*, 182:90–94 (1985).
Laemmli and Favre, "Maturation of the Head of Bacteriophage T4", *J.Mol.Biol.*, 80:575–599 (1973).
T. Maniatis, et al., *Molecular Cloning, A Laboratory Manual*, Cold Spring Harbor Press: Cold Spring Harbor, NY (1982).
Mullis and Faloona, "Specific Synthesis of DNA in Vitro via a Polymerase–Catalyzed Chain Reaction", *Meth., Enzymol.* 155:335–350 (1987).
Nagata, et al., "Synthesis in *E. coli* of a polypeptide with human leukocyte interferon activity", *Nature,* 284:316–320 (1980).
Parekh, et al., "Cell–Type–Specific and Site–Specific N–Glycosylation of Type II Human Tissue Plasminogen Activator", *Biochemistry*, 28:7644–7662 (1989).

(List continued on next page.)

Primary Examiner—Robert A. Wax
Assistant Examiner—Kawai Lau
Attorney, Agent, or Firm—Marshall, O'Toole, Gerstein, Murray & Borun

[57] ABSTRACT

This invention relates to improved fungal cells and methods for producing recombinant products of improved quality and in high yields. More specifically, the present invention relates to fungal cells carrying specific modifications within their DNA sequences which cause them to exhibit at least a reduced capacity for O-glycosylating homologous and/or heterologous proteins, and the use of these cells as host cells to produce high yields of recombinant products.

22 Claims, 10 Drawing Sheets

OTHER PUBLICATIONS

Roberts and Lauer, "Maximizing Gene Expression on a Plasmid Using Recombination in Vitro", *Meth., Enzymol.* 68:473–382 (1979).

Romanos, et al., "Foreign Gene Expression in Yeast: a Review", *Yeast*, 8:423–488 (1992).

Rothstein, "Targeting, Disruption, Replacement, and Allele Rescue: Integrative DNA Transformation in Yeast", *Meth. Enzymol.* 194:281–301 (1991).

Saiki, et al., "Enzymatic Amplification of β–Globin Genomic Sequences and Restriction Site Analysis for Diagnosis of Sickle Cell anemia", *Science*, 230:1350–1354 (1985).

Sambrook, et al., *Molecular Cloning, A Laboratory Manual*, Second edition, Cold Spring H Press: Cold Spring Harbor, NY (1989).

Sanger, et al., "DNA sequencing with chain–terminating inhibitors", *Proc.Natl.Acad.Sci. (USA)* 74:5463–5467, (1977).

Saunders, et al., "Secretion of Human Serum Albumin for *Bacillus subtilis*", *J.Bacteriol*, 169:2917–2925 (1987).

Sengstag and Hinnen, "The sequence of the *Saccharomyces cervisiae* gene PH02 codes for a regulatory protein with unusual aminoacid composition", *Nuc.AicdsRes.*, 15:233–246 (1987).

Settineri et al., "Charaterization of O–Glycosylation Sites in Recombinant B–Chain of Platelet–derived Growth Factor Expressed in Yeast Using Liquid Secondary Ion mass Spectrometry, Tandem Mass Spectometry and Edman Sequence Analysis", *Biomedic.Environ.Mass Spectroscopy*, 19:655–676 (1990).

Sherman, *Methods in Yeast Genetics*, CSH Press (1986) p. 127.

Stahl, "The Macrophage mannose Receptor: Current Status", *Cell.Mol.Biol.* 2:317–318 (1990).

Strahl–Bolsinger and Tanner, "Protein O–glycosylation in *Saccharomyces cerevisiae* —Purification and characterization of the dolichl–phosphate–D–mannose–protein O–D–mannosyltranferase", *Eur.J.Biochem.* 196:185–190 (1991).

Takeuchi, et al., "Relationship between sugar chain structure and biological activity of recombinant human erythropoietin produced in chinese hamster ovary cells", *Proc.Natl.Acad. Sci. (USA)*, 86:7819–7822 (1989).

Van dr Berg, et al., "Kluyveromyces as a host heterologous gene expression: expression and secretion of prochymosin", *Bio/Technology*, 8:135–139 (1990).

Häusler,et al., "Yeast glycoprotein biosynthesis: MNT1 encodes an α–1.2–mannosyltransferase involved in O–glycosylation", *Proc.Natl'l.Acad.Sci. (USA)*, 89:6846–6850 (1992).

Montell, C. et al. (1988) "The Drosophila ninaC locus encodes two phtoreceptor cell specific proteins with domains homoglous to protein kinases and the myosin heavy chain head" *Cell* 52(5):757–772.

Farkas, V. et al. (1976) "Biosythesis of yeast mannan. Characterization of mannan–synthesizing enzyme systems from mutants defective in mannan structure" *Folia Microbiol.* . 21(6):459–464.

Farkas et al. as previously cited.

Fig.4A

SEQ ID NO :1

TYPE OF SEQUENCE:   Nucleotides
LENGTH:   3375 base pairs
NUMBER OF STRANDS:   1
CONFIGURATION:   Linear
TYPE OF MOLECULE:   cDNA
ORIGIN :   Saccharomyces cerevisiae

```
  1  GCTTGTCTCC TGTTCATTCT ACGCTTGTCA TCCACACTGG CACCGGCAGC
 51  GGCGCTGCTC TGTGAGCTGT CTTTATCCAG CAGGCTCAAA TAGACTTGTT
101  CTGCCTCATA TACTGTTTTT CATTAACCAG TCTCCTGGCC TCTTCTAATT
151  TCGAACCTGG CAGAGACATG AAGTTCCTCG TTATAGATTA ATCACCAATT
201  GTCCTCTTTC AGCGCTTCTG TTAGTTGGCC TTATTTAACG GATCTTTGCT
251  TCAATTACGC TTTCATCCAA CATTTGCCAC CCTTGGAACC AGAAGAGAAT
301  ATACATCATT CGGGGTTGCC CTGCCCATTT ATATCGTATA TTGTGATGAT
351  ATACCTTTTT TTTTTTTTTC GCTGCGTTTT TTTTCTCGAC ACGTGTCGAA
401  GAAGAGTTTG GCGTTTCTAA GCAGATCTTG ATTATTTTCG AGCAGCAAAA
451  CAAGACAAAC AGGTGCATTG TTAAAGCGAG GTAGTATCAG AAGAGCCTAT
501  CAAGAAACAG CTAACAGCTA CAAGCACGGT C<u>ATG</u>TCGGAA GAGAAAACGT
551  ACAAACGTGT AGAGCAGG<u>AT</u> <u>G</u>ATCCCGTGC CGAACTGGA TATCAAGCAG
601  GGCCCCGTAA GACCCTTTAT TGTTACCGAT CCGAGTGCCG AATTGGCCTC
651  GTTACGAACC ATGGTCACTC TTAAAGAGAA GCTGTTAGTG GCCTGTCTTG
701  CTGTCTTTAC AGCGGTCATT AGATTGCATG GCTTGGCATG GCCTGACAGC
751  GTGGTGTTTG ATGAAGTACA TTTCGGTGGG TTTGCCTCGC AATACATTAG
801  GGGGACTTAC TTCATGGATG TGCATCCTCC TCTTGCAAAG ATGTTGTATG
851  CTGGTGTGGC ATCGCTTGGT GGGTTCCAGG GTGATTTTGA CTTCGAAAAT
901  ATTGGTGACA GCTTTCCATC TACGACGCCA TACGTGTTGA TGAGATTTTT
```

```
 951  CTCTGCTTCT  TTGGGGGCTC  TTACTGTTAT  TTTGATGTAC  ATGACTTTAC
1001  GTTATTCTGG  TGTTCGTATG  TGGGTTGCTT  TGATGAGCGC  TATCTGCTTT
1051  GCCGTTGAAA  ACTCGTACGT  CACTATTTCT  CGTTACATTC  TGTTGGACGC
1101  CCCATTGATG  TTTTTCATTG  CAGCTGCAGT  CTACTCTTTC  AAGAAATACG
1151  AAATGTACCC  TGCCAACTCG  CTCAATGCTT  ACAAGTCCTT  GCTTGCTACT
1201  GGTATTGCTC  TTGGTATGGC  ATCTTCATCC  AAATGGGTTG  GTCTTTTCAC
1251  GGTTACATGG  GTGGGTCTTT  TATGTATCTG  GAGACTATGG  TTCATGATTG
1301  GGGATTTGAC  TAAGTCTTCC  AAGTCCATCT  TCAAAGTAGC  ATTTGCCAAA
1351  TTGGCCTTCT  TGTTGGGTGT  GCCTTTTGCC  CTTTATCTGG  TCTTCTTTTA
1401  TATCCACTTC  CAATCATTAA  CTTTGGACGG  GGATGGCGCA  AGCTTCTTTT
1451  CGCCTGAATT  TAGATCTACA  CTAAAGAACA  ATAAGATCCC  CCAAAATGTC
1501  GTTGCTGATG  TCGGCATTGG  CTCCATTATC  AGCTTGCGTC  ATCTCTCTAC
1551  CATGGGCGGT  TATTTGCATT  CTCATTCACA  CAATTATCCA  GCTGGTTCGG
1601  AACAACAACA  AAGCACTTTA  TATCCTCACA  TGGATGCCAA  TAACGATTGG
1651  TTGTTGGAAC  TTTACAACGC  ACCCGGCGAA  TCTTTAACAA  CATTCCAAAA
1701  CCTAACCGAT  GGTACCAAGG  TCAGACTATT  CCACACTGTT  ACAAGATGTA
1751  GATTACACTC  TCATGACCAT  AAGCCACCCG  TTTCAGAAAG  CAGCGACTGG
1801  CAGAAGGAGG  TTTCTTGTTA  TGGTTACAGC  GGATTCGACG  GTGATGCTAA
1851  TGATGACTGG  GTTGTTGAGA  TTGATAAAAA  GAATTCTGCT  CCTGGAGTTG
1901  CCCAAGAACG  GGTCATAGCT  TTGGACACAA  AGTTTAGATT  GAGACATGCT
1951  ATGACAGGCT  GTTATTTGTT  TTCCCACGAA  GTCAAGTTGC  CAGCTTGGGG
2001  GTTCGAACAA  CAAGAAGTTA  CCTGTGCCTC  CTCCGGTAGA  CATGATTTAA
2051  CATTGTGGTA  CGTTGAGAAC  AACAGTAACC  CATTGTTACC  AGAAGATACC
2101  AAGCGTATTT  CCTATAAACC  TGCAAGCTTC  ATTTCTAAAT  TTATTGAATC
2151  CCATAAAAAG  ATGTGGCATA  TCAATAAAAA  TTTGGTCGAA  CCTCATGTTT
2201  ATGAATCACA  ACCAACTTCA  TGGCCATTCT  TGCTACGTGG  TATAAGTTAC
2251  TGGGGTGAAA  ATAACAGAAA  CGTCTATCTA  TTAGGTAATG  CGATCGTATG
2301  GTGGGCTGTC  ACCGCTTTCA  TCGGTATTTT  CGGATTGATT  GTTATCACTG
```

```
2351 AGCTGTTCTC GTGGCAGTTA GGTAAACCAA TTTTGAAGGA CTCCAAGGTT
2401 GTTAACTTCC ACGTTCAGGT TATTCACTAC TTATTGGGTT TTGCCGTCCA
2451 TTATGCTCCA TCTTTCTTAA TGCAACGTCA AATGTTTTTG CATCACTACT
2501 TACCTGCTTA TTATTTCGGT ATTCTTGCCC TTGGCCACGC CTTGGACATA
2551 ATAGTTTCTT ATGTTTTCCG CAGCAAGAGA CAAATGGGCT ACGCGGTAGT
2601 GATCACTTTC CTTGCTGCTT CTGTGTATTT CTTCAAGAGC TTCAGTCCAA
2651 TTATTTACGG TACACCATGG ACTCAAGAAT TGTGTCAAAA ATCGCAGTGG
2701 TTGTCTGGTT GGGACTACAA TTGTAACACA TACTTTTCTT CATTAGAAGA
2751 GTACAAAAAC CAAACCTTGA CTAAACGTGA ATCTCAACCT GCCGCCACTA
2801 GTACAGTTGA AGAAATCACT ATAGAAGGGG ACGGTCCGTC GTATGAAGAT
2851 CTCATGAACG AGGATGGCAA GAAAATCTTT AAAGACACAG AAGGTAATGA
2901 ACTAGATCCA GAAGTTGTCA AAAAAATGTT GGAAGAGGAG GGAGCTAACA
2951 TTTTAAAAGT AGAAAAAGG GCTGTTTGG AATAAATTTC CCAGTACTCT
3001 CCACATTTTT ATGTAAAGTC TTCTATAAGC TCTCGAGCGT ATAATTAAAA
3051 ACGAAAATAG ACAAAAAAA CATCATGAAT AAAAAAAATG TCTTGAAGCT
3101 GACTATATTG TCCATCTGCG TTTAGAGACA CGTATTCTAT TTCGCTCAAA
3151 TAAGTATGAT CTGCAAGTAG TTTCAGTGGT ATTATCATTT CGCACCGTTT
3201 TTTTTCCAAG AACTCGTTTA CGTGCCGCGA AAAGTCTATC GAATAGGCAT
3251 TCGAGAACAA TAGAAAAGGA ACAGAAGCGT AGTACATATT ATGCATAGAC
3301 CCGTTTCTTT TCTTCTTTTT CGAAAATATT CTTATTGATT TAACAATTAA
3351 GCAGGTGTGT AAGATCAGAA CTGCA
```

SEQ ID NO: 2

TYPE OF SEQUENCE:     Peptidic
LENGTH :              817 amino acids
PROPERTY:             Dol-P-Man:protein(Ser/Thr)Mannosyltransferase
ORIGIN:               Saccharomyces cerevisiae

```
  1   MSEEKTYKRV  EQDDPVPELD  IKQGPVRPFI  VTDPSAELAS  LRTMVTLKEK
 51   LLVACLAVFT  AVIRLHGLAW  PDSVVFDEVH  FGGFASQYIR  GTYFMDVHPP
101   LAKMLYAGVA  SLGGFQGDFD  FENIGDSFPS  TTPYVLMRFF  SASLGALTVI
151   LMYMTLRYSG  VRMWVALMSA  ICFAVENSYV  TISRYILLDA  PLMFFIAAAV
201   YSFKKYEMYP  ANSLNAYKSL  LATGIALGMA  SSSKWVGLFT  VTWVGLLCIW
251   RLWFMIGDLT  KSSKSIFKVA  FAKLAFLLGV  PFALYLVFFY  IHFQSLTLDG
301   DGASFFSPEF  RSTLKNNKIP  QNVVADVGIG  SIISLRHLST  MGGYLHSHSH
351   NYPAGSEQQQ  STLYPHMDAN  NDWLLELYNA  PGESLTTFQN  LTDGTKVRLF
401   HTVTRCRLHS  HDHKPPVSES  SDWQKEVSCY  GYSGFDGDAN  DDWVVEIDKK
451   NSAPGVAQER  VIALDTKFRL  RHAMTGCYLF  SHEVKLPAWG  FEQQEVTCAS
501   SGRHDLTLWY  VENNSNPLLP  EDTKRISYKP  ASFISKFIES  HKKMWHINKN
551   LVEPHVYESQ  PTSWPFLLRG  ISYWGENNRN  VYLLGNAIVW  WAVTAFIGIF
601   GLIVITELFS  WQLGKPILKD  SKVVNFHVQV  IHYLLGFAVH  YAPSFLMQRQ
651   MFLHHYLPAY  YFGILALGHA  LDIIVSYVFR  SKRQMGYAVV  ITFLAASVYF
701   FKSFSPIIYG  TPWTQELCQK  SQWLSGWDYN  CNTYFSSLEE  YKNQTLTKRE
751   SQPAATSTVE  EITIEGDGPS  YEDLMNEDGK  KIFKDTEGNE  LDPEVVKKML
801   EEEGANILKV  EKRAVLE
```

Fig.4B

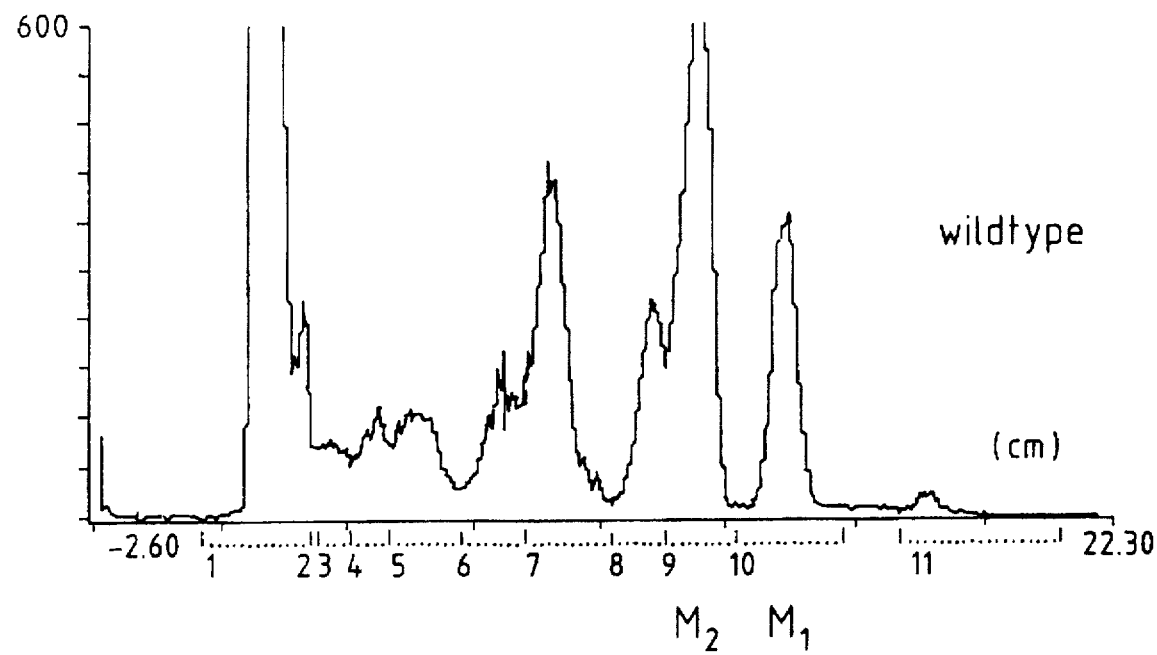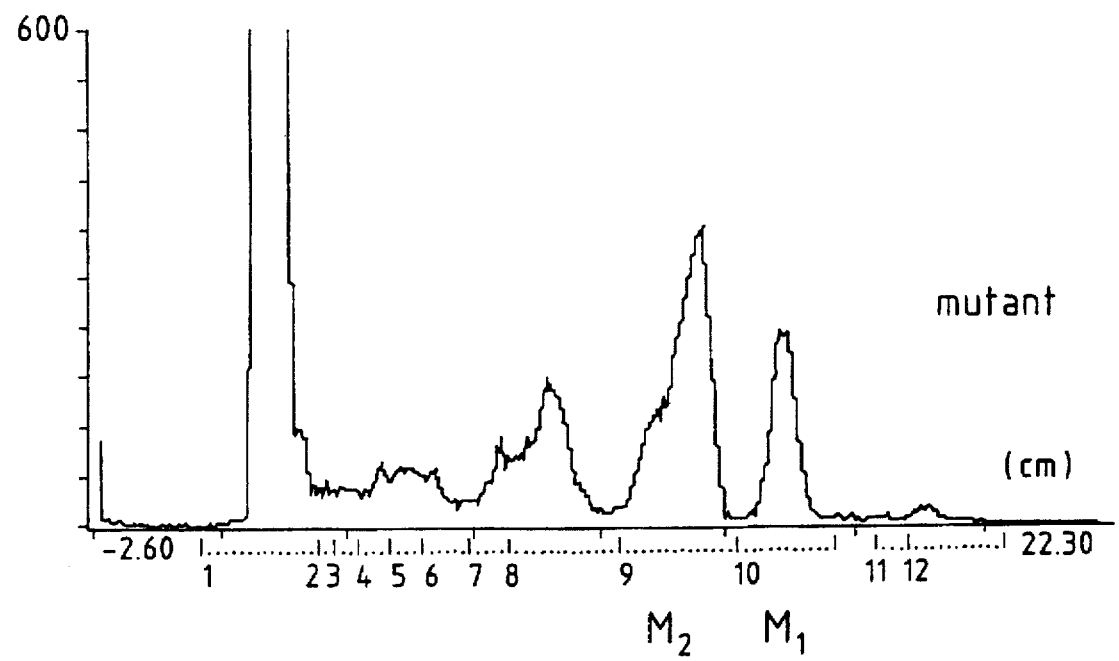
Fig. 6

SEQ ID No. 3

| | |
|---|---|
| Sequence Type: | DNA |
| Sequence Length: | 126 base pairs |
| Topology: | linear |
| Strandedness: | single |
| Feature: | part of the K. lactis Dol-P-Man:protein (Ser/Thr) mannosyltransferase encoding gene (open reading frame) |
| Origin: | Kluyveromyces lactis |

```
  1 TCTGCTCCTG GCGNAGCTCA AGTATNCGTT AAGGCTTTGG ACACTAAATT
 51 CAGATTGAGA CATGCTATGA CTGGTTGTAG TATCTCACAT GAAGTCAAAT
101 TACCAAAATG GGGCTTCGAA CAACAG
```

Fig. 7

(A)

position 1885 of SEQ. ID N° 1

```
TCTGCTCCT  GGAGTTGCC  CAAGAACGG  GTCATAGCT  TTGGACACA  AAGTTTAGA
.........  .. .  ..   .... .     .. . ...   ........   .. .. ...
TCTGCTCCT  GGCG?AGCT  CAAGTAT?C  GTTAAGGCT  TTGGACACT  AAATTCAGA

TTGAGACAT  GCTATGACA  GGCTGTTAT  TTGTTTTCC  CACGAAGTC  AAGTTGCCA
.........  ........   .. ... .   .   ..     .. ......  .. .. ...
TTGAGACAT  GCTATGACT  GGTTGTAGT  ATC---TCA  CATGAAGTC  AAATTACCA

GCTTGGGGG  TTCGAACAA  CAA
.....      .........  ..
AAATGGGGC  TTCGAACAA  CAG
```

(B)

position 452 of SEQ. ID N° 2

```
SAPGVAQER  VIALDTKFR  LRHAMTGCY  LFSHEVKLP  AWGFEQQ
.... ..    . .......  .........  .......    ......
SAPG?AQV?  VKALDTKFR  LRHAMTGCS  I-SHEVKLP  KWGFEQQ
```

Fig. 8

MODIFIED FUNGAL CELLS AND METHOD FOR PRODUCING RECOMBINANT PRODUCTS

This invention relates to improved fungal cells and methods for producing recombinant products of improved quality and in high yields. More specifically, the present invention relates to fungal cells carrying specific modifications within their DNA sequences which cause them to exhibit at least a reduced capacity for O-glycosylating homologous and/or heterologous proteins, and the use of these cells as host cells to produce high yields of recombinant products.

The development of recombinant DNA technology has made possible the production of foreign products in host cells in which exogenous DNA sequences coding for those products have been introduced. The advantage of this technology is that products can be produced in high yields, in highly purified form, with no risk of contamination such as viral contamination (AIDS, hepatitis B, etc.). These recombinant techniques have been widely used for the production of recombinant proteins in prokaryotic as well as eukaryotic host cells. Prokaryotic host cells include *E. coli* [Nagata et al., Nature 284(1980), 316; EP 001 929], *Bacillus subtilis* [Saunders et al., J. Bacteriol. 169 (1987), 2917], Streptomyces, and Corynebacterium (EP 433 117). Eukaryotic host cells include plant cells, animal cells and fungal cells.

However, the large-scale production of recombinant products by these techniques is still limited, due to problems of expression efficiency of these exogenous DNA sequences, due also to vector instability and to intracellular degradation of the recombinant products by the host cell in which they are made. Concerning expression efficiency, efforts have been made to isolate strong promoters, leading to increased expression levels of exogenous DNA sequences, and therefore to increased production levels of recombinant products. Various systems have also been developed in order to increase the stability of the vectors within the host cells, the most frequently used of which consisting in the insertion on the vector of an antibiotic resistance gene enabling recombinant host cells to survive and grow in a selective medium. With respect to intracellular degradation, several mutant cells lacking or having a reduced protease activity have been disclosed, thereby limiting the capacity of said cells to degrade recombinant products.

However, additional problems still limit large-scale production and pharmaceutical use of recombinant products. One of these arises from the fact that recombinantly produced products are often different from their natural counterparts. For example, bacterial host cells do not possess all the post-translational mechanisms required for maturation of mammalian polypeptides. Accordingly, said mammalian polypeptides produced in bacteria are often immature or not correctly refolded. Furthermore, bacterial host cells generally introduce an additional N-terminal methionine to the products.

Recombinant products produced in heterologous eukaryotic hosts also usually differ from their naturally-occurring counterpart in their glycosylation content. This may concern the presence versus absence of any carbohydrate structure, the localization of said carbohydrate structure on the product, as well as the nature of the carbohydrate. More specifically, it has been shown that yeast-derived recombinant products often bear additional unnatural O-glycans compared to their natural counterpart. For instance, it has been shown that, while human serum insulin-like growth factor I (IGF-I) is not glycosylated, its recombinant form produced in *S. cerevisiae* is O-glycosylated and, more precisely, O-mannosylated [Hard et al., FEBS Letters 248 (1989), 111]. In the same way, it has been shown that human platelet-derived growth factor (PDGF) and human GM-CSF display unnatural O-mannosyl structures when produced in *S. cerevisiae* [Biomedic. Environ. Mass Spectrometry 19 (1990), 665; BIO/TECHNOLOGY 5 (1987), 831]. This abnormal O-glycosylation is the result of important differences between the glycosylation mechanisms of mammalian (human) cells and those of other eukaryotic cells, such as yeasts. In this respect, it has been observed that O-glycosylation in fungal cells (including yeasts and filamentous fungi) proceeds in a similar and unusual way so far not observed in any other organism.

The occurrence of this undesirable O-glycosylation on fungal-derived recombinant products constitutes an important drawback to this technology for the production of pharmaceuticals.

The first reason is that fungal-specific glycans may introduce new immunological determinants on a protein, and a glycoprotein with such unnatural carbohydrates may therefore be antigenic when administered to humans. In this respect, it is known for example that most humans have antibodies directed against N-linked yeast mannan chains [Feizi and Childs, Biochem. J. 245 (1987), 1].

Another reason is that proteins without appropriate carbohydrate structures may also have altered pharmacokinetic properties. It has been shown that carbohydrate structures of glycoproteins influence and participate in defining their in vivo clearance rate, which is essential in determining the efficacy of a pharmaceutical. More precisely, a mannose receptor has been identified on the surface of liver endothelial cells and resident macrophages which apparently represents a means for eliminating glycoproteins displaying mannose-type oligosaccharides [Stahl, Cell. Mol. Biol. 2 (1990), 317]. Therefore, the presence of unnatural, additional mannose structures on a protein may increase its clearance rate and thus decrease its plasma half life.

Still another reason is that biological activity of a glycoprotein has also been shown to vary with its carbohydrate content, location and nature. For example, it has been shown that glycosylation affects the biological properties of recombinant human EPO [Takeuchi et al., Proc. Natl. Acad. Sci. USA 86 (1989), 7819]and recombinant human tPA [Parekh et al., Biochemistry 28 (1989), 7644].

For the reasons mentioned above, it is clear that the unnatural O-glycosylation of fungal-derived recombinant products can severely affect their immunological, biological and pharmacokinetic properties, and therefore may prevent their development for human therapeutic use.

The present invention solves the problem of abnormal O-glycosylation referred to above by providing modified fungal cells carrying genetic modification(s) within their DNA sequences which cause them to have at least a reduced capacity for O-glycosylating native or foreign proteins.

Applicant has found that it is possible to obtain genetically modified fungal cells having reduced capacity of O-glycosylation which are still viable and show good growth characteristics in industrial fermentation conditions. Unexpectedly, Applicant has also shown that said genetic modifications do not affect stability of these fungal cells when transformed with exogenous DNA. The modified fungal cells of the present invention can be utilized advantageously as host cells for the production of recombinant products of high quality, having reduced or no undesirable O-glycans.

One object of the present invention is a fungal cell carrying genetic modification(s) within its DNA sequences which cause it to have at least a reduced capacity of O-glycosylation.

The fungal cell of the present invention can be chosen from filamentous fungi and yeasts. Exemplary genera of filamentous fungi contemplated by the present invention are Aspergillus, Trichoderma, Mucor, Neurospora, Fusarium and the like. Exemplary genera of yeasts include Kluyveromyces, Saccharomyces, Pichia, Hansenula, Candida, Schizosaccharomyces and the like. More preferred genera are those selected from the group consisting of Kluyveromyces, Saccharomyces, Pichia, Hansenula and Candida, and, even more preferred, from Kluyveromyces and Saccharomyces. Exemplary strains of Kluyveromyces which constitute preferred embodiments of this invention include *K. lactis, K. fragilis, K. waltii, K. drosophilarum* and the like. The preferred strain of Saccharomyces is *S. cerevisiae*.

In the meaning of the present invention, genetic modification preferably means any suppression, substitution, deletion or addition of one or more bases or of a fragment of the fungal cell DNA sequences. Such genetic modifications may be obtained in vitro (directly on isolated DNA) or in situ, for example by genetic engineering techniques or by exposing the fungal cells to mutagenic agents. Mutagenic agents include for example physical agents such as energetic rays (X-rays, χ-rays, UV, etc.) or chemical agents capable of reacting with different functional groups of DNA, such as alkylating agents (EMS, NQO, etc.) bisalkylating agents, intercalating agents, etc. Genetic modifications may also be obtained by genetic disruption, for example according to the method disclosed by Rothstein et al. [Meth. Enzymol. 194 (1991), 281–301].

According to this method, part or all of a gene is replaced, through homologous recombination, by an in vitro modified version.

Genetic modifications can also be obtained by any mutational insertion on DNA sequences, such as transposons, phages, etc.

In addition, it is known that certain modifications such as point mutations can be reversed or attenuated by cellular mechanisms. Such modifications may not provide the most useful forms of modified fungal cells of this invention since their phenotypical properties may not be very stable. The present invention also provides a process for preparing modified fungal cells in which the modifications (and therefore the phenotypical properties) are stable during segregation and/or non-reverting and/or non-leaky. Such modified fungal cells are particularly advantageous as hosts for the production of recombinant products.

Accordingly, a preferred embodiment of the invention is a fungal cell carrying genetic modification(s) which are stable during segregation and/or non-reverting and/or non-leaky. These modifications are generally obtained by deletion(s) or disruption(s).

The genetic modification(s) carried by the fungal cells of the invention can be located either in a coding region of the DNA sequences of the cell or in a region responsible for or involved in the expression and/or transcriptional regulation of a gene. More particularly, said modification(s) will generally affect the coding region or the region responsible for or involved in the expression and/or the transcriptional regulation of one or more genes whose expression products are enzymes of the O-glycosylation pathway.

The reduced capacity of the fungal cells of the invention to O-glycosylate proteins may therefore result from the production of inactive enzymes due to structural and/or conformational changes, from the production of enzymes having altered biological properties, from the absence of production of said enzymes, or from the production of said enzymes at low levels.

The fungal cell O-glycosylation pathway involves attachment of a first mannosyl residue to the hydroxyl group of seryl and/or threonyl amino acids of proteins or peptides, and then the extension to O-linked di- and oligosaccharides by subsequent addition of mannosyl residues. The first mannosyl residue is transferred from dolichol monophosphate mannose (Dol-P-Man) to the protein in the endoplasmic reticulum, and the additional mannosyl residues are transferred from GPD-Man in the Golgi. In contrast, higher eukaryotic (non-fungal) cells O-glycosylate following a different mechanism, in that the initial step is the covalent attachment of N-acetyl-galactosamine to seryl or threonyl amino acids, no lipid-coupled oligosaccharide donor is involved in this first reaction, the initial step occurs in the Golgi, the structures of carbohydrates are different, etc.

In a preferred embodiment of the invention, the modified fungal cells carry genetic modification(s) in at least one gene whose expression product is involved in the attachment of a mannosyl residue to the hydroxyl group of seryl or threonyl amino acids.

In a more preferred embodiment of the invention, the modified fungal cells carry genetic modification(s) in at least one gene whose expression product is involved in the transfer of a mannosyl residue from the Dol-P-Man precursor to the hydroxyl group of seryl or threonyl amino acids.

Still more preferably, one of these genes is the gene encoding the Dol-P-Man:Protein (Ser/Thr) Mannosyl Transferase [DPM2-also designated PMT1] whose sequence is represented in FIG. 4, or any homologous gene encoding the same activity as defined below.

In addition to modification(s) in one gene involved in the attachment of mannosyl residues to the hydroxyl group of seryl or threonyl amino acids, fungal cells of the invention may also carry modification(s) in the genes involved in subsequent additions of mannosyl residues leading to di- or oligosaccharides, or in the synthesis of the mannosyl residues donnor (Dol-P-Man).

Specific examples of such fungal cells are disclosed in the examples.

Another object of the invention resides in a fungal cell as disclosed above in which an exogenous DNA sequence has been introduced.

In the meaning of the present invention, the term exogenous DNA sequence includes any DNA sequence comprising one or more genes encoding a desired protein to be expressed and/or secreted in said cell. Such a DNA sequence may be a complementary DNA sequence (cDNA), an artificial DNA sequence, a genomic DNA sequence, a hybrid DNA sequence or a synthetic or semi-synthetic DNA sequence, included in an expression cassette enabling synthesis in the fungal cells of said proteins. The expression cassette preferably comprises a transcription and translation initiation region joined to the 5' end of the sequence encoding said desired protein(s) so as to direct, and optionally regulate, the transcription and translation of said sequence. The choice of these regions may vary according to the fungal cell used. Generally, these sequences are chosen from promoters and/or terminators derived from fungal cell genes, and, when expression in yeast hosts is sought, from yeast genes. Of special interest are certain promoter and/or terminator regions derived from glycolytic genes of fungal cells such as, for yeasts, the genes encoding phosphoglycerate kinase (PGK), glyceraldehyde-3-phosphate dehydrogenase (GDP), enolases (ENO) or alcohol dehydrogenases (ADH), and for filamentous fungi, the genes encoding triose phosphate isomerase (tpi). The promoter and/or terminator regions may also derive from other strongly expressed genes such as, for yeasts, the lactase gene (LAC4), the acid phosphatase gene (PHO5), the alcohol oxidase gene (AOX) or the methanol oxidase gene (MOX), and, for filamentous fungi, the cellobiohydrolase gene (CBHI), the alcohol dehydrogenase gene (alcA, alcC), the glucoamylase gene (GAM) or the acetamidase gene (amds), and the like. These transcription and translation initiation regions may be further modified, e.g. by in vitro mutagenesis, by introduction of additional control elements or synthetic sequences, or by deletions. For example, transcription-regulating elements, such as the so-called UAS, originating from another promoter may be used to construct hybrid promoters which enable the growth phase of the fungal cell culture to be separated from the phase of expression of the desired protein(s) encoding sequence(s). A transcription and translation termination region functional in the intended fungal cell may also be positioned at the 3' end of the coding sequence. In addition, at the N-terminus of the protein sequence, a signal peptide (pre-sequence) may be introduced so as to direct the nascent protein to the secretory pathway of the fungal cell used. This pre-sequence may correspond to the natural pre-sequence of the protein if this protein is naturally secreted, or it may be of another origin, e.g. obtained from another gene, or even artificial.

Preferably, the exogenous DNA sequence is part of a vector, which may either replicate autonomously in the fungal cell used or integrate into its own DNA sequences (chromosome). Autonomously replicating vectors may contain autonomously replicating sequences derived from the chromosomal DNA of the fungal cell (ARS) or from naturally-occurring fungal cell plasmids such as pGKl-1 [de Louvencourt et al., J. Bacteriol. 154 (1982), 737], pKD1 (EP 241 435), 2 μm plasmid (Broach, Cell 28 (1982), 203–204) and the like. Integrating vectors usually contain sequences homologous to regions of the fungal cell chromosome which, after being introduced into said cell, enable integration through in vivo recombination. In a specific embodiment of the invention, said homologous sequences correspond to the region of the chromosome to be modified in the fungal cell, enabling a one-step modification-integration mechanism. Integration may also occur through non-homologous recombination.

The exogenous DNA sequence can be introduced into the fungal cell by any technique known in the art, and, for example, by recombinant DNA techniques, genetic crossings, protoplast fusions, etc. Concerning recombinant DNA techniques, transformation, electroporation, or any other technique disclosed in the literature may be used. More specifically, when the fungal cell is a yeast cell, the transformation may be performed according to the methods of Ito et al., [J. Bacteriol. 153 (1983), 163], Durrens et al. [Curr. Genet. 18 (1990), 7] or following the method disclosed in EP 361 991. Electroporation can be performed according to Karube et al. [FEBS Letters 82 (1985), 90].

The fungal cells of the present invention can be advantageously utilized as host cells for the production of recombinant products such as heterologous proteins having pharmaceutical and/or agro-foodstuff interest. The fungal cells of this invention are particularly advantageous since they enable the production and/or secretion of high quality products, and since their genetic modifications do not affect the mitotic or genetic stability of said products' expression vectors. The cells of this invention are more particularly suitable for the production of proteins having human therapeutic uses and which are susceptible to O-glycosylation by the host cell.

Accordingly, a further object of this invention resides in a process for the production of recombinant products wherein a fungal cell as defined above is cultivated in conditions in which the exogenous DNA sequence is expressed and the product is recovered. In a preferred embodiment, said product is secreted into the culture medium. In another preferred embodiment, said product is susceptible to O-glycosylation by the host cell.

The following proteins are cited as examples of heterologous proteins which can be prepared with the fungal cells of the present invention: enzymes (such as superoxide dismutase, catalase, amylases, lipases, amidases, chymosine, etc., or any fragment or derivative thereof), blood derivatives (such as human serum-albumin, alpha- or beta-globin, factor VIII, factor IX, van Willebrand factor, fibronectin, alpha-1 antitrypsin, etc., or any fragment or derivative thereof), insulin and its variants, lymphokines [such as interleukins, interferons, colony stimulating factors (G-CSF, GM-CSF, M-CSF . . . ), TNF, TRF, etc., or any fragment or derivative thereof], growth factors (such as growth hormone, erythropoietin, FGF, EGF, PDGF, TGF, etc., or any fragment or derivative thereof), apolipoproteins, antigenic polypeptides for the preparation of vaccines (hepatitis, cytomegalovirus, Eppstein-Barr, herpes, etc.), or any fusion polypeptide such as, for example, fusions comprising an active moiety linked to a stabilizing moiety.

Another object of the invention resides in a DNA fragment encoding an enzyme involved in the attachment of mannosyl residues to the hydroxyl group of seryl or threonyl amino acids of proteins. Applicant has provided DNA fragments encoding such enzymes for the first time. More preferably, said DNA fragment comprises the Dol-P-Man:Protein (Ser/Thr) mannosyltransferase gene whose sequence is represented in FIG. 4, any homologous gene, derivative or fragment thereof.

In the meaning of the present invention, homologous gene means any other gene of any fungal cell encoding an enzyme having the required activity. Said other genes may be obtained, for example, by complementation of a mutant fungal cell deficient in said activity with DNA prepared from a fungal cell capable of said activity, selection of the transformants having recovered the activity, and isolating their inserted DNA sequence. These other genes may also be isolated from DNA libraries by hybridization with probe(s) (including PCR primers) comprising all or part of the sequence presented in FIG. 4. In this respect, it is also an object of this invention to use the DNA fragments provided, or any part thereof, as hybridization probe(s) or for the complementation of mutant phenotypes, for the obtention of homologous genes of fungal cells.

The term derivative means any other DNA fragment prepared by any genetic and/or chemical modification(s) of the genes mentioned above. Said genetic and/or chemical modification(s) may be any suppression, substitution, deletion or addition of one or more bases or of a region of said genes, leading either to an increased enzyme activity or to the same activity level, or to a decreased or null enzyme activity upon transformation in a fungal host cell.

LEGEND OF THE FIGURES

FIG. 1: Restriction map of plasmids pDM3, pMT4 and pMT1.

Figure 2:
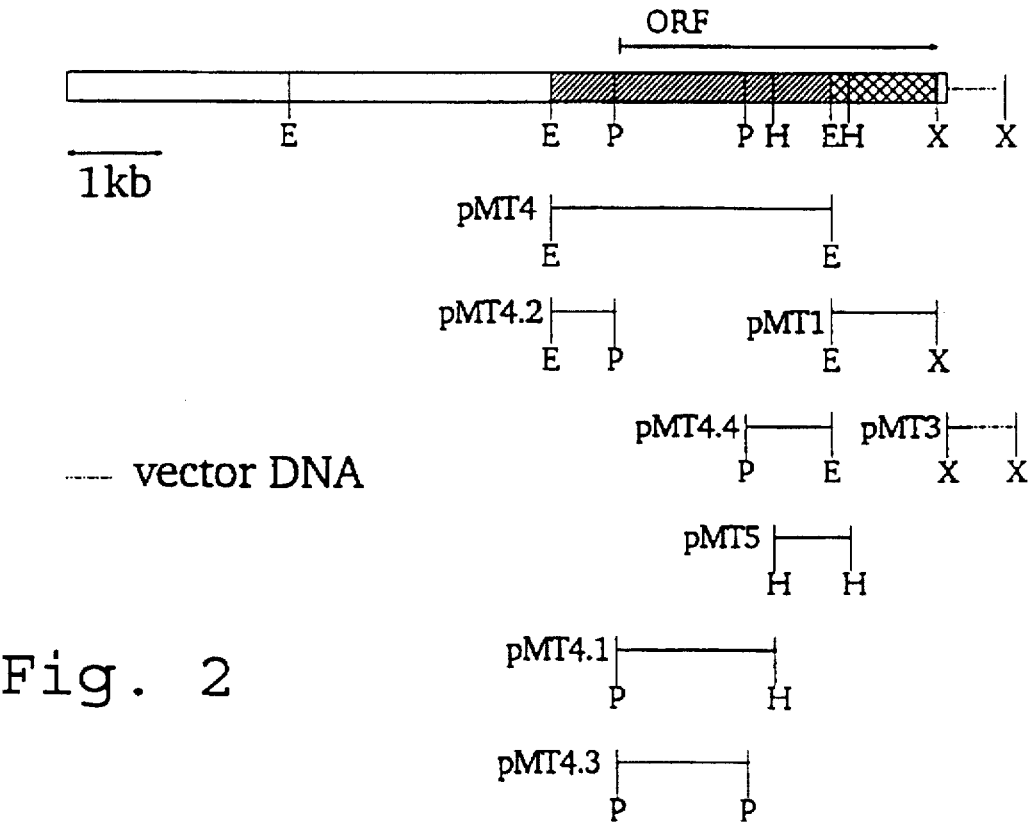

FIG. 2: Subcloning of plasmid pDM3.

Figure 3:
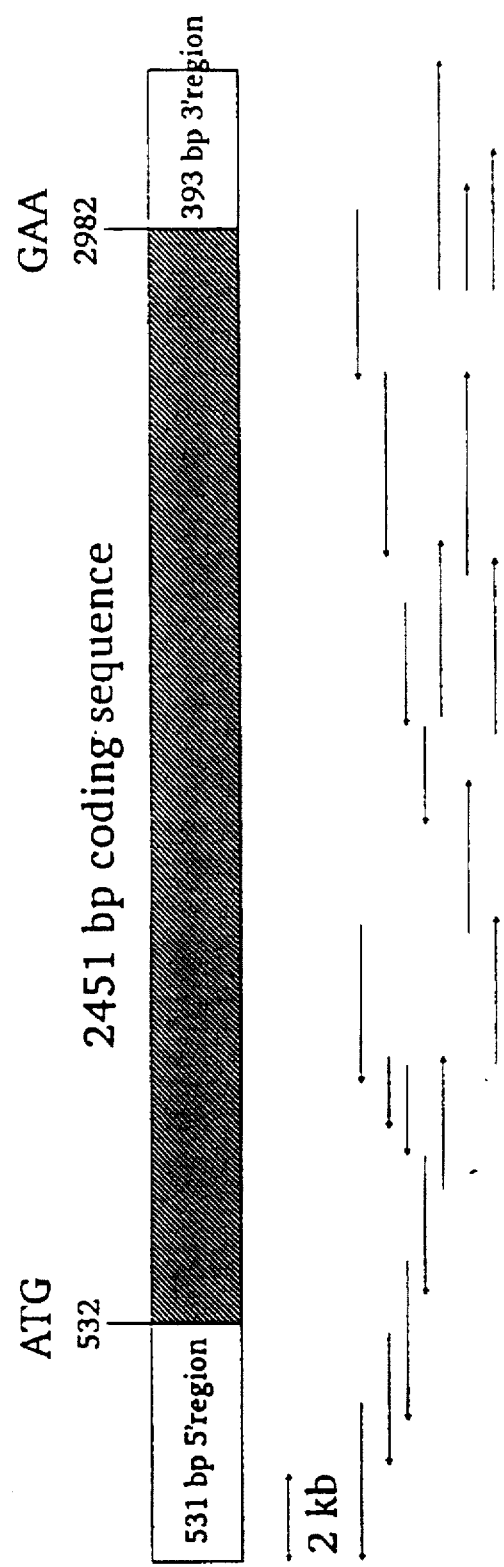

FIG. 3: Strategy of sequencing of the PMT1 gene.

FIG. 4a: Nucleotide sequence of the PMT1 gene (SEQ ID N°1).

FIG. 4b: Amino acid sequence of the PMT1 gene (SEQ ID N°2).

Figure 5:
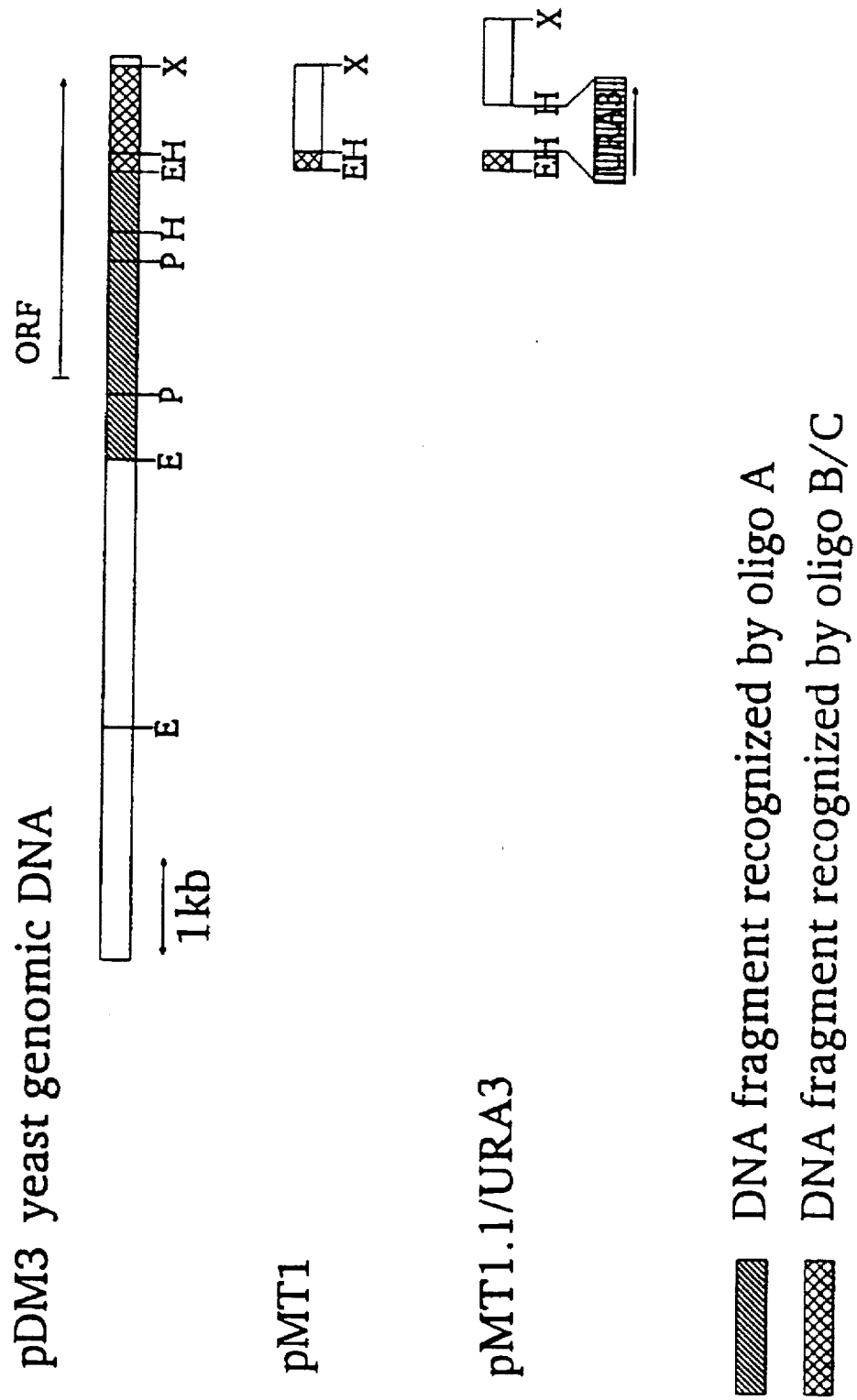

FIG. 5: Construction and restriction map of pMT1.1/URA3.

FIG. 6: O-glycosylation activity of S. cerevisiae WT (panel A) and MT (panel B).

FIG. 7: Partial nucleotide sequence of the K. lactis PMT1 gene (SEQ ID No. 3).

FIG. 8: Nucleotide (Panel A) and predicted amino acid (Panel B) sequence comparison between the S. cerevisiae PMT1 gene (upper sequences) and the K. lactis homolog (lower sequences) isolated by PCR amplification of K. lactis genomic DNA. Dots represent sequence identity, question marks indicate sequence ambiguity. The nucleotide sequence complementary to the primer Sq3910 is underlined.

EXAMPLES

Example 1

Isolation of a highly purified mannosyltransferase from S. cerevisiae and generation of peptides The mannosyltransferase activity was solubilized from total yeast membranes and purified on hydroxylapatite according to Strahl-Bolsinger and Tanner (Eur. J. Biochem. 196 (1991), 185). The protein then had to be further enriched by $(NH_4)_2SO_4$ precipitation before additional purification was performed via affinity chromatography. The eluted material was then separated on SDS/PAGE. The resulting 92 kDa band was cut out of the gel. Trypsin digestion (in the gel) yielded several non-overlapping peptides, enabling designing of probes.

E.1.1. $(NH_4)_2SO_4$ precipitation 100 ml of fractions of the hydroxylapatite column containing mannosyltransferase activity was mixed with $(NH_4)_2SO_4$ up to a final concentration of 30% (w/v) and stirred gently for 1 h in an ice/salt bath. The mixture was centrifuged for 30' (8000×g). The resulting pellet was resuspended in 8 ml AB-buffer (10 mM Tris/HCl, pH 7.5, 15% glycerol (vol %), 0.1% lubrol (vol %), 150 mM NaCl) and dialyzed for 1 h against the same buffer. Storage: −20° C.

E.1.2. Affinity chromatography

E.1.2.1. Preparation of the affinity chromatography column 0.5 g freeze-dried powder of Protein A-Sepharose Cl4B was swollen in 10 ml 100 mM NaPi, pH 7.0, for 15' and washed on a sintered glass filter (G3) with 200 ml of the same buffer. Protein A-Sepharose Cl4B was equilibrated in 100 mM NaPi, pH 7.0. About 3 to 6 ml antimannosyltransferase serum was dialyzed for 2 h against 1 l NaPi (100 mM), pH 7.0. The dialyzed serum was incubated with the column material for 16 h at 4° C. The serum was removed using a sintered glass filter (G3). The column material was washed twice with 10 ml 100 mM NaPi, pH 8.5, and resuspended in 50 ml of the same buffer.

For covalent coupling 0.75 mg/ml dimethylsuberimidate was added. The pH was adjusted to pH 8.5 by adding 5–6 drops of 1M NaOH. The material was incubated for 1 h at RT. For a second time, dimethylsuberimidate was added and the pH adjusted to pH 8.5 with 1M NaOH. The column material was washed serially on a sintered glass filter (G3) with:

a) 50 ml 100 mM NaPi, pH 8.0
b) 25 ml 100 mM NaPi, pH 8.0, 3M ammonium rhodanide
c) 100 ml 100 mM NaPi, pH 8.0

The material was washed and equilibrated in AB-buffer.

E.1.2.2. Purification of the 92 kDa protein 8 ml of the $(NH_4)_2SO_4$ precipitated and dialyzed protein (E.1.1.) was incubated with the affinity column material (E.1.2.1) for 16 h at 4° C. with gentle shaking. A column (2 cm×0.5 cm) was filled and washed with 15 ml AB-buffer. The column was eluted with 100 mM glycine/HCl pH 3.0, 0.05% lubrol (vol %), 15% glycerol (vol %). Fractions of 0.9 ml were collected and neutralized immediately with 1M Tris (15 µl/0.9 ml fraction).

To detect the 92 kDa protein, 40 µl of each eluted fraction was analyzed by SDS/PAGE and Western-blot analysis as described (Strahl-Bolsinger and Tanner, 1991). The 92 kDa protein containing fractions (fraction 2–6) were pooled and concentrated to 100 µl via microconcentrators (Centricon/Amicon) by centrifugation at 5000×g. 0.9 ml 98% EtOH were added and the protein precipitated for 16 h at −20° C. The precipitated protein was pelleted by centrifugation for 30' at 10,000×g.

E.1.3. SDS-PAGE

The precipitated protein (E.1.2.2) was resuspended in 150 µl SDS-sample buffer (0.07M $Na_2CO_3$, 0.07% β-EtSH, 2% SDS, 12% Saccharose, 0.07% bromphenolblue). SDS-gel electrophoresis according to Lämmli and Favre [J. Mol. Biol. 80 (1973), 575] was carried out at 50–70 V using the BIORAD-Mini-Protean cell. Protein standards: HMW-Standards/Gibco BRL.

Protein was detected by staining with 0.05% Coomassie R250 (w/v), 25% isopropanol (vol %), 10% acetic acid (vol %) and destaining in 7.5% acetic acid (vol %).

E.1.4 Trypsin digestion and designing of oligonucleotides

After SDS-PAGE (E.1.3.) the 92 kDa protein band was cut out (about 10 µg of protein). The gel fragment was cut into small pieces and shaken three times for 30' in 5 ml 50% methanol/10% acetic acid and one time for 30' in 5 ml 50% methanol. The gel was lyophylized for 3 h. Trypsin digestion was carried out in 0.3 ml 0.2M ammoniumhydrogen carbonate/2µg trypsin for 16 h at 37° C. Supernatant was removed. Elution of the peptides was done three times for 1 h at 37° C. in 0.2 ml 0.2M ammoniumhydrogen carbonate and one time for 1 h at 37° C. in 0.2 ml 0.2M ammoniumhydrogen carbonate/30% acetonitrile. The eluted material was pooled, lyophylized and resolved in 0.2 ml 1M guanidinium hydrochloride/50 mM Tris/HCl pH 7.5. Peptides were separated using a reverse phase RP18 column equilibrated in 0.13% TFA. Peptides were eluted by acetonitrile (0–70%). Up to 40 different peptide peaks could be detected. Five of the main peaks were sequenced via automated sequence analysis according to Edman (G. Allen in: Sequencing of proteins and peptides, Laboratory Techniques in Biochem. and Mol. Biol. 9 ed.: Burdon, R. H. & Knippenberg, P. H.; Elsevier (1989)). Among the sequences thereby obtained, three were suitable for designing oligonucleotides, which are presented in Table 1, below.

TABLE 1

| Peak | Peptide Sequence |
|---|---|
| 15 | I S Y K P A S F I S K |
| 23 | E V S P Y G Y S G F D G D A |
| 34 | N L V E P H V Y E S |

On the basis of these sequences, oligonucleotides A–C were chemically synthesized, using the codon usage of S. cerevisiae (Guthrie and Abelson in: The molecular biology of the yeast Saccharomyces; eds: J. N. Strathern, E. W. Jones, J. R. Broach (1982)). Oligonucleotides A–C have the following characteristics:

Oligonucleotide A:
  peak: 23
  amino acid sequence: G F D G D A
  Oligodeoxynucleotide: 5'-G$^T/_C$GTCACCGTCGAANCC-3'
  8-fold degenerated, coding strand, 17 nucleotides Oligonucleotide B:
  Peak: 34
  Amino acid sequence: E P H V Y E
  DNA sequence: 5'-$^C/_T$TCGTAGAC$^G/_A$TG$^A/_T$GG$^T/_C$TC-3'
  16-fold degenerated, coding strand, 18 nucleotides Oligonucleotide C:
  Peak: 15
  Amino acid sequence: I S Y K P A S F I S K
  DNA sequence: 5'-ATTTC$^T/_A$TA$^T/_C$AA$^A/_G$CC$^A/_T$GCTTC$^T/_A$TT$^T/_A$AAA-3'
  128-fold degenerated, coding strand, 33 nucleotides

Example 2

Screening of a plasmid library of yeast genomic DNA

The chemically synthesized oligodeoxynucleotides A–C (E.1.4.) were used to screen the plasmid library of yeast genomic DNA pCS19 (Sengstag and Hinnen, Nucl. Acids Res. 15 (1987), 233). This library was prepared by partial digestion of yeast genomic DNA with Sau3A, and cloning into the BclI restriction site of the vector pCS19.

E.2.1. Labeling of Oligodeoxynucleotides

The oligonucleotides A–C were labeled by kinase reaction, carried out according to Maniatis et al (T. Maniatis, J. Sambrook, E. F. Fritsch (1989), Molecular cloning: A Laboratory manual, C.S.H. Press). 40 pmol Oligodeoxynucleotide were labeled using 50 µCi [γ-$^{32}$P]-ATP. Free radioactive nucleotides were removed using "NUC Trap Push columns" (Stratagene) according to the instruction manual of the producer.

E.2.2. Screening of the library

The DNA-library (4992 different single colonies) was transferred from microtiterplates to nitrocellulose. Colony hybridization was performed according to Grunstein and Hogness (PNAS 72 (1975), 3961) in the following conditions:

Prehybridization: Filters were incubated at 44° C. in 200 ml 5×Denhardt's, 6×NET, 0.1% SDS (w/v), 0.1 mg/ml salmon sperm DNA, for at least 4 h (5×Denhardt's: 0.1% ficoll, 0.1% polyvinylpyrrolidone, 0.1% BSA; 6×NET: 0.9M NaCl 90 mM Tris-HCl pH 8.3, 6 mM EDTA, pH 8.0).

Hybridization: Filters were incubated at 44° C. in 100 ml 5×Denhardt's, 6×NET, 0.1% SDS (w/v), 0.1 mg/ml salmon sperm DNA, labeled oligodeoxynucleotides A and B (40 pmol each). Hybridization was performed for 16 h.

washing conditions: Filters were washed three times in 50 ml 6×SSC, 0.1% SDS (w/v) at 0° C. for 15'.

To detect positive colonies, the filters were exposed to X-ray films for 16 h, −70° C. Under these conditions, 12 positively reacting clones could be identified.

Example 3

Southern Analysis of the 12 positive clones

The 12 positive clones were analyzed in Southern blots using three different oligodeoxynucleotides. This analysis led to the identification of one positive clone reacting with all three oligonucleotides. This clone was called pDM3.

The 12 positive clones were grown in 5 ml LB medium supplemented with ampicillin and their DNA was isolated according to the method of Birnbaum and Doly (Nucl. Acid. Res. 7, (1979), 1513).

¹/₁₀ of each isolated plasmid DNA (plasmids: pDM1–pDM12) was digested with the restriction enzymes EcoRI-XhoI (5 U each), 1×"one for all" buffer (Pharmacia) in a total volume of 20 µl for 1 h at 37° C. DNA fragments were separated on a 1% agarose gel and blotted to nitrocellulose according to Maniatis etal. (loc. cit.). Southern analysis was performed using oligo A and B using the same conditions as described for the library screen. The hybridization temperature for oligo A was 48° C., for oligo B 42° C. Clones 1, 2, 3, 5, 6, 7 and 11 reacted positively with both oligodeoxynucleotides. These seven clones were further analyzed by Southern blot analyses. Three identical blots were therefore prepared, in which the DNA of clones 1, 2, 3, 5, 6, 7 and 11 was digested with EcoRI-XhoI and blotted to nitrocellulose as described. Blots 1, 2 and 3 were prehybridized in 20 ml 5×Denhardt's, 6×NET, 0.1% SDS (w/v), 0.1 mg/ml salmon sperm DNA at 50° C. for 4 h. Each blot was then hybridized in 10 ml 5×Denhardt's, 6×NET, 0.1% SDS (w/v), 0.1 mg/ml salmon sperm DNA, 40 pmol labeled oligonucleotides for 16 h. The hybridization temperature is indicated in Table 2, below. Washing was performed for 10' at each temperature in 50 ml 2×SSC, 0.1% SDS (w/v).

TABLE 2

| Blot | Hybridization with oligo | Hybridization temperature | Washing conditions | Positive reacting clones |
| --- | --- | --- | --- | --- |
| Blot 1 | A | 25 | 2x10'/25° C. 1x10'/35° C. | 1, 2, 3, 5, 6, 7, 11 |
| Blot 2 | B | 25 | 2x10'/25° C. 1x10'/35° C. | 3, 5 |
| Blot 3 | C | 45 | 2x10'/45° C. 1x10'/55° C. | 3 |

Clone 3 was the only clone reacting with oligo A, B and C. The clone was called pDM3 and further analyzed.

Example 4

Analysis of pDM3

E.4.1. Methods

E.4.1.1 Digestion with restriction endonucleases

Analytic digestion with endonucleases was performed in 1×"one for all" buffer (Pharmacia), 0.2–0.5 µg of DNA, 1–5 U restriction enzyme in a total volume of 20 µl for 1 h at 37° C.

Preparative digestion was performed in a total volume of 40–80 µl with 1–10 µg of DNA, 5–20 µl restriction enzyme, 1×"one for all" buffer for 2 h at 37° C.

E.4.1.2. DNA-gelelectrophoresis

Separation of DNA fragments was performed according to Maniatis et al. (loc. cit.).

E.4.1.3. Isolation of DNA fragments

After separation, DNA fragments were isolated using the "Gene-clean kit" (Stratagene) according to the instruction manual of the producer.

E.4.1.4. Treatment with alkaline phosphatase

DNA fragments were dephosphorylated with alkaline phosphatase according to Maniatis et al. (loc. cit.).

E.4.1.5. Ligation

DNA fragments were ligated in 1×T4-ligation buffer (50 mM Tris/HCl pH 7.5, 10 mM MgCl$_2$, 5 mM DTT, 1 mM ATP) with 1 U T4-DNA ligase (total volume 10–15 µl ). Molar DNA ratio of vector: insert was 1:4 or 1:8. The absolute amount of DNA was 20–50 ng. Incubation time: 16 h at 14° C. or 5 h at 25°C.

E.4.1.6. Transformation of E. coli

Competent E. coli DH5α cells were prepared according to Hanahan (J. Mol. Biol. 166 (1983), 557). Transformation was carried out as described by Maniatis et al. (loc. cit.).

E.4.1.7. Preparation of DNA

Plasmid DNA was prepared according to Birnbaum and Doly (loc. cit.).

E.4.1.8. Southern blot analysis

Southern blot analysis was performed using the same condition as described in E.3.

E.4.1.9. DNA sequence analysis

DNA sequencing was done according to the method of Sanger et al. (PNAS 74 (1977), 5463). Only plasmid DNA was sequenced. T7-DNA polymerase sequencing kit (Pharmacia) was used; the radioactive nucleotide was [α-$^{35}$S]-dATP (spec. act. 600 Ci/mmol).

E.4.2. Identification of the ORF

This example discloses a restriction analysis of pDM3, the identification of different DNA fragments recognized by oligonucleotides A, B or C and their subcloning. Sequencing of these subclones enabled identification of an ORF.

E.4.2.1. Subcloning of pDM3 DNA fragments hybridizing with oligo A, B or C.

pDM3 DNA was digested with EcoRI, XhoI and EcoRI-XhoI. Southern blot analysis was performed using oligo A, B or C as a target.

Oligo A recognizes a 3.0 kb EcoRI fragment, oligo B and C recognize a 1.1 kb EcoRI-XhoI fragment. The 3.0 kb EcoRI fragment was subcloned into pUC19 (linearized with EcoRI and dephosphorylated). The 1.1 kb EcoRI-XhoI fragment was subcloned into pUC18 (linearized with EcoRI-SalI, and dephosphorylated). Right subclones were identified by restriction analyses and Southern blot analysis using oligo A or B/C, respectively.

The 3.0 kb EcoRI subclone was called pMT4, the 1.1 kb EcoRI-XhoI subclone was called pMT1. Further restriction analysis of pMT4 and pMT1 was performed using a number of different restriction endonucleases (for example: PstI, HindIII and BglII). Southern blot analysis using oligo A or B/C was carried out to define the exact region of a possible ORF.

Restriction maps of pDM3, pMT4 and pMT1 are shown on FIG. 1.

E.4.2.2. Sequence analysis

From both ends, the DNA inserts of plasmids pMT4 and pMT1 were sequenced using the universal and reverse primers, priming next to the polylinker of pUC19/pUC18. Also oligos A, B and C were used as sequencing primers. The sequencing data resulted in an ORF of about 400 bp on both sides of the insert of pMT1. Also pMT4 showed an ORF of about 200 bp when sequenced with the reverse primer. Using these sequencing data, an amino acid sequence could be deduced. This AA-sequence showed peptide sequences known from the peptide analysis of the 92 kDa protein (peptides corresponding to peaks 15, 23, 34 were found). According to these data, the 5'/3' orientation of the gene could be predicted.

Several other subclones were constructed and sequenced using the universal and reverse primers of pUC18/19 (FIG. 2).

The following oligodeoxynucleotides were also used for sequencing:

| Oligo | Sequence (5'–3') | vector sequenced |
|---|---|---|
| Oligo 6 | CCAACCAGACAACCACTGGG 2713 | pMT1 |
| Oligo 7 | GACAGGCCACTAACAGCTTC 697 | pMT4 |
| Oligo 8 | GATGTTGTATGCTGGTGTG 840 | pMT4 |
| Oligo 9 | CATTGAGCGAGTTGGCAGGG 1178 | pMT4 |
| Oligo 4 | GAACCTCATGTTTATGAA 2189 | pMT1 |

These oligodeoxynucleotides represent parts of the newly sequenced DNA fragments.

For sequencing the 5' region of the gene, exoIII/mung bean deletions of the vector pMT4 were made. pMT4 was linearized using SphI (3' overlap). The plasmid was then cut using BamHI (5' overlap).

Exonuclease III deletion was performed according to Roberts and Lauer (Meth. Enzymol. 68 (1979), 473), Henikoff (Meth. Enzymol. 155 (1987), 156).

Overlapping ends were removed by mung bean nuclease. The resulting plasmids were analyzed by restriction analysis using HindIII and EcoRI.

Sequence analysis of the clones was carried out using the reverse primer of pUC19. The sequence strategy is shown in FIG. 3. Sequence data are given in FIG. 4.

Example 5

Northern blot analysis: Identification of mRNA encoding Mannosyltransferase.

E.5.1. Methods

E.5.1.1. Isolation of RNA

Total RNA was isolated from yeast strain SEY2101 (Mat a, ade2-1, leu2-3, 112, ura3-52 (Emr et al. PNAS 80 (1983), 7080) according to Domdey et al. (Cell 39 (1984), 611).

E.5.1.2. Northern blot

Total RNA was separated using a formaldehyde agarose gel and blotted to nitrocellulose as described by Maniatis et al. (loc. cit.).

E.5.1.3. The DNA-target

The 1.1 kb insert of pMT1 was isolated by EcoRI-PstI digestion. The fragment was purified using the "Gene-clean kit" (Stratagene).

200 ng of the DNA fragment were labeled with [α-$^{32}$P]-dCTP (50 µCi) using the "megaprime" labeling kit (Amersham) according to the instruction manual of the producer.

E.5.2. Results

The nitrocellulose filter was prehybridized for 2 h at 42° C. in 20 ml 5×Denhardt's, 2×SSC, 0.1% SDS (w/v), 50% formamide (v/v), 0.1 mg/ml salmon sperm DNA. Hybridization was performed at 42° C. for 16 h in 10 ml 1×Denhardt's, 2×SSC, 0.1% SDS (w/v), 50% formamide (v/v), 0.1 mg/ml salmon sperm DNA, 200 µg [α-$^{32}$P]-dCTP labeled 1.1 kb EcoRI-PstI fragment of pMT1. Washing was done twice at RT and two times at 50° C. in 50 ml 0.1×SSC, 0.1% SDS (w/v). Hybridization of the target was detected by exposure to X-ray film (−70° C., 16 h). A single mRNA with the size of 3 kb was detected.

This procedure may be easily repeated by the person skilled in the art with other probes derived from the sequence of FIG. 4 and with RNA from other sources (other fungal cells).

Example 6

Preparation of an *S. cerevisiae* cell deficient in O-glycosylation activity.

An *S. cerevisiae* cell deficient in O-glycosylation activity was prepared by gene disruption, by insertion of the URA3 gene into the HindIII restriction site of the identified ORF, at bp 1595 of the coding sequence.

E.6.1. Construction of the plasmid used for the gene disruption

The 1.1 kb insert of pMT1 was isolated as EcoRI-PstI fragment and subcloned into a pUC18 vector (EcoRI/PstI linearized, dephosphorylated, without HindIII restriction site in the polylinker). The resulting vector was called pMTI.1.

pMT1.1 was linearized with HindIII and dephosphorylated. The 1.1 kb HindIII fragment of YEp24 (Julius et al., Cell 37 (1984), 1075) containing the URA3 gene of *S. cerevisiae* was isolated and subcloned into the HindIII linearized, dephosphorylated vector pMT1.1. Clones were identified by restriction analyses and called pMT1.1/URA3 (FIG. 5).

pMT1.1/URA3 has 0.24 kb PMT1 coding sequence flanking one side of the URA3 gene and 0.86 kb PMT1 coding sequence flanking the other. CsCl-DNA of pMT1.1/URA3 was prepared according to Maniatis et al. (loc. cit.).

E.6.2. Transformation of yeast

40 µg of pMT1.1/URA3 CsCl-DNA was digested with SphI/EcoRI. To check that the digestion was complete, part of the digested DNA was analyzed on a DNA agarose gel. The digest was then phenolized and the DNA precipitated with 98% EtOH (Maniatis et al., loc. cit.). DNA was resolved in 10 µl TE, pH 8.0.

*S. cerevisiae* strains SEY2101/2102 (Mat a/αura3-52, leu2-3, 112 (Emr et al., loc. cit.) and SEY2101 (Mat a, ura3-52, leu2-3, 112, ade2-1) were transformed with 5 µl of the EcoRI/SphI digested vector pMT1.1/URA3 according to the method of Ito et al. (J. Bacteriol. 153 (1983), 163).

SEY2101/2102 transformants were selected on minimal media +Leu; SEY2101 transformants were selected on minimal media+Leu, +Ade.

After 3–4 days at 30° C., transformants could be picked and plated on the same media for a second time.

E.6.3. Genomic Southern blot of the transformants

Genomic DNA of three haploid transformants and wild-type cells was isolated as described by Hoffmann and Winston (Gene 57 (1987), 267). 1 µg of the genomic DNA was digested with XhoI/EcoRI, separated on an agarose gel and blotted to nitrocellulose as described by Maniatis et al. (loc. cit.).

The blot was prehybridized in 20 ml 5×Denhardt's, 2×SSC, 0.1% SDS (w/v), 0.1 mg/ml salmon sperm DNA, 50% formamide (w/v) for 4 h at 42° C.

Hybridization was permitted in 10 ml of the same solution adding 200 ng [α-$^{32}$P]-dCTP labeled 1.1 kb EcoRI/PstI fragment of pMT1.1 (see: E.5.1.3) for 16 h at 42° C. Washing was done two times at RT in 50 ml 2×SSC, 0.1% SDS (w/v) and two times at 68° C. in 50 ml 1×SSC, 0.1% SDS (w/v). Signal detection by X-ray films. Wild-type cells showed a single signal at 1.1 kb, reflecting the EcoRI/XhoI fragment without URA3 insertion. In the disrupted strains this signal was missing. Instead of this, a new 2.2 kb fragment was recognized by the 1.1 kb target, representing the 1.1 kb EcoRI/XhoI fragment bearing the 1.1 kb URA3 insertion.

Example 7

Characterization of the mutant

E.7.1. Growth

SEY2101 wild-type cells were grown either on YPD (10 g/l yeast extract; 10 g/l peptone; 20 g/l dextrose) or on minimal media+Ade, +Leu, +Ura. SEY2101 PMT1::URA3 mutant cells were grown either on YPD or on minimal media+Ade, +Leu. Cells were grown at 30° C. in a waterbath shaker. OD578 was measured every 30' after sonifying cells. Wild-type and mutant cells show nearly identical growth on both media although, in some cases, mutant cells may stick together. Nevertheless, such cells can easily be separated by sonifying (30", sonify water bath). The growth characteristics of these cells are listed below:

Generation time:
WT: 99'
MT: 93'
Cell number:
WT: 1 OD=1.9×10$^7$
MT: 1 OD=1.9×10$^7$
Doubling rate:
WT: 0.61/h
MT: 0.65/h In a logarithmically growing culture, 54.7% of wild-type cells and 56% of mutant cells show buds. After growing for 24 h on YPD wild-type cells reached an OD578 of 11.4 and mutant cells of 12.3.

E.7.2. In vitro mannosyltransferase activity and Western blot
E.7.2.1. Preparation of crude membranes SEY2101 was grown in 100 ml minimal media+Ade+Leu+Ura to OD578=0.5. SEY2101 PMT1::URA3 was grown in 100 ml minimal media+Ade, +Leu to OD578=0.5.

Two preparations of each strain were carried out. Work was performed on ice; all buffers were at 4° C. 40 OD of cells were pelleted and washed in 25 ml TMA (50 mM Tris/HCl pH 7.5, 7.5 mM MgCl$_2$). Cells were resuspended in 100 µl TMA and transferred to a violax tube. 0.3 g of glass beads were added and cells broken on a vortex four times for 30" (cooling on ice between breaking intervals). The extract is removed from glass beads using a pasteur pipette. Glass beads are washed three times with 250 µl TMA. All washing solutions are pooled in an Eppendorf cup. The solution is centrifuged for 15" (10,000×g). Supernatant is removed and the pellet resuspended in 40 µl TMA (1 OD=1 µl)

E.7.2.2. Mannosyltransferase assay (in vitro)

1 and 5 µl of the crude membranes (E.7.2.1) were tested for enzyme activity as described by Strahl-Bolsinger and Tanner (loc. cit.). Two parallel samples from wild-type and mutant cells were measured. Mean values of these two independent measurements are shown.

|    | µl membranes | cpm/incubation[1] |
| --- | --- | --- |
| WT | 1 | 2786 |
| WT | 5 | 10289 |
| MT | 1 | 563 |
| MT | 5 | 1135 |

[1] Control values (without peptide) were 506 and 1031, respectively.

In contrast to wild-type cells, mutant cells show no in vitro mannosyltransferase activity.

E.7.2.3. Western blot analysis

Membranes (1 µl of E.7.2.1) were incubated in 20 µl SDS sample buffer for 1 h at RT. Then SDS/Page and western blot were performed as described by Strahl-Bolsinger and Tanner (loc. cit.). For antibody detection the Peroxidase ECL kit (Amersham) was used according to the instruction manual of the producer. Antibodies against the 92 kDa protein react specifically with a 92 kDa protein of wild-type membranes. In mutant membranes this 92 kDa signal is missing.

E. 7.3. In vivo O-glycosylation

To investigate in vivo glycosylation, wild-type and mutant cells were grown in the presence of [$^3$H]-mannose. Then a crude cell wall plus membrane fraction was isolated and O-glycosylated material released by β-elimination.

E.7.3.1 Treatment with [$^3$H]-mannose

Wild-type and mutant cells were grown over night in minimal media containing sucrose as only C-source. 7.5 OD of the culture (OD578=1–2) were pelleted and washed with 5 ml H$_2$O (prewarmed 30° C.). The cells were grown in 5 ml YP/0.5% sucrose/250 μCi [$^3$H]-mannose in a waterbath shaker for 2 h at 30° C.

E.7.3.2. Isolation of crude cell wall and membrane fraction

5 OD of the [$^3$H]-mannose treated cells were centrifuged and washed three times with 1 ml TMA. Cells were resuspended in 200 μl TMA and broken with glass beads as described in E.7.2.1 (10 μl sample was used for counting radioactivity corresponding to total incorporation). The extract was then centrifuged for 15' (10,000×g) and the supernatant was removed (100 μl sample was used for counting radioactivity corresponding to soluble material).

E.7.3.3. β-elimination

The pellet was resuspended in 1 ml 0.1N NaOH (a 10 μl sample was used for counting radioactivity corresponding to material before β-elimination). Incubation was maintained for 24 h at 30° C.

E.7.3.4. Analysis of β-eliminated material

β-eliminated material was desalted via a Dowex 50WS8/H$^+$ column (0.5cm×6cm). The column was saturated with 0.5M mannose and equilibrated in H$_2$O. The β-elimination sample was loaded onto the column and washed through with 1.5 μl H$_2$O. The flow through was collected (a 100 μl sample was used for counting radioactivity corresponding to β-eliminated material) and concentrated to 10 μl in the speed-vac. Thin-layer chromatography on Silicagel 60 (Merck) in acetone:butanol:H$_2$O 70:15:15 was performed. Standards: mannose, sucrose, stachyose, raffinose. The chromatographic run was repeated once. Sugars were detected with 0.5 g KMnO$_4$ in 100 ml 1N NaOH. Radioactivity was detected by a thin-layer scanner (Berthold) (see FIG. 6).

| Cell/cpm | Total incorporation | Soluble material | Material before β-elimination | β-eliminated radioactivity |
|---|---|---|---|---|
| WT | 1.46 × 10$^7$ | 2.23 × 10$^6$ | 1.2 × 10$^7$ | 1.2 × 10$^6$ |
| MT | 1.12 × 10$^7$ | 1.84 × 10$^6$ | 0.79 × 10$^7$ | 4.0 × 10$^5$ |

Mutant cells show reduced glycosylation in comparison to wild-type cells. The O-glycosylation in mutant cells is about 40–50% lower than in wild-type cells.

Example 8

Cloning of the PMT1 homolog of *Kluyveromyces lactis*.

The yeast *S. cerevisiae* used to be the system of choice when the production of a heterologous protein in a fungal host cell was desired. However, recent years have shown that the productivity of bakers yeast is often limited, especially when the secretion of the product to the culture medium is required. The use of fungal systems other than *S. cerevisiae* is therefore preferable in a number of cases [c.f. Romanos et al., Yeast 8 (1992) 423–488; Fleer, Curr. Opinion Biotechnol. 3 (1992) 486–496]. One of the alternative yeast hosts is represented by the genus Kluyveromyces for which superior secretion yields have been found with respect to several proteins of commercial interest [e.g. Van den Berg et al., Bio/Technology 8 (1990) 135–139]. The following example demonstrates that the present invention is not limited to bakers yeast, since the sequence of the PMT1 gene isolated from *S. cerevisiae* can be advantageously used for the identification of genes encoding similar enzymatic activities in other fungal species. Furthermore, the sequence information revealed in the present invention may also be used for the identification of related mannosyltransferase encoding genes in *S. cerevisiae*.

E.8.1. Design of degenerate PCR primers for the amplification of PMT1 related genes The region of the PMT1 nucleotide sequence corresponding to the central, hydrophilic region of the mannosyltransferase protein was chosen to design PCR primers [Polymerase-catalyzed Chain Reaction, Saiki et al., Science 230(1985) 1350–1354; Mullis & Faloona, Meth. Enzymol. 155 (1987) 335–350] for the amplification of homologous genes. Amplification requires hybridization, also termed annealing, of these synthetic oligonucleotides with its target DNA. The specificity with which individual regions of genomic DNA are amplified depends on the conditions of the PCR reaction and the degree of homology between the primers and the nucleotide sequence to be amplified. Subsequent to the annealing step, the primers are extended using a thermostable DNA polymerase. Once the complementary strand has been polymerized, the two strands are separated by heat denaturation and a new cycle of annealing and polymerization may begin.

Four examples of oligonucleotides suitable as primers for PCR amplification of PMT1 homologs are presented in Table 2 below.

TABLE 2

| Primer Designation | Nucleotide Sequence |
|---|---|
| Sq3908 SEQ ID NO: 4 | 5'-ATGGAYGCNAAYAAYGAYTGG-3' |
| Sq3909 SEQ ID NO: 5 | 5'-GAYGCNAAYGAYGAYTGGGT-3' |
| Sq3910 SEQ ID NO: 6 | 5'-TCYTGYTGYTCRAANCCCCA-3' |
| Sq3911 SEQ ID NO: 7 | 5'-CTRTTRTTYTCNCCCCARTA-3' |

The design of these "degenerate" oligonucleotides takes into account that several codons may contain the information for the incorporation of the same amino acid into a nascent polypeptide chain, most often varying in the third ("wobble") position of a triplet. Each primer therefore represents a mixture of oligonucleotides where Y signifies C or T, R signifies A or G, and N signifies A, C, G or T.

E.8.2. PCR amplification of *K. lactis* genomic DNA

Genomic DNA of *K lactis* strain CBS2359 was prepared as described by Sherman et al. ["Methods in Yeast Genetics", Cold Spring Harbor Laboratory Press (1986) p 127]. 10 ng of genomic DNA were used in a standard PCR reaction [Sambrock et al., "Molecular Cloning—A Laboratory Manual", second edition, Cold Spring Harbor Laboratory Press (1989)] in the presence of 1 μg of each of the primers and 5% deionized formamide. The amplification was performed using a "DNA Thermal Cycler" (Perkin Elmer Cetus) and "AmpliTaq DNA Polymerase" (Perkin Elmer Cetus, 5 units per reaction tube). The conditions for denaturation, annealing, and polymerization (30 cycles) were 91° C. (1 min), 42° C. (2 min), and 72° C. (3 min), respectively, except for the first cycle where denaturation was for 5 min. The results of the PCR amplifications using the primers disclosed above are presented in Table 3 below.

TABLE 3

| Primer Combinations | Approx. size of amplified DNA DNA fragments (bp) | |
|---|---|---|
| | expected for PMT1 homolog | observed |
| Sq3908+Sq3910 | 400 | 400 |
| Sq3908+Sq3911 | 600 | 600 |
| Sq3909+Sq3910 | 170 | 170 |
| | 300 | |
| Sq3909+Sq3911 | 400 | 400 |
| | 800 | |

These results show that it is not only possible to obtain fragments exhibiting the same size as that expected for the K. lactis homolog of the S. cerevisiae PMT1 gene but that, in addition, DNA fragments can be amplified with high specificity that most likely correspond to another gene coding for a closely related enzymatic activity.

E.8.3 Partial sequence characterization of the K. lactis PMT1 homolog

The 400 bp fragment amplified with the primer combination sq3908+Sq3910 was subcloned into the vector pCRII (TA Cloning™, Invitrogen Corp.) following the indications of the supplier, and partially sequenced according to the method described in E.4.1.9. using the universal primer. The sequence obtained is presented in FIG. 7. Sequence comparison between the S. cerevisiae PMT1 gene and the fragment isolated from K. lactis genomic DNA by PCR amplification reveals 75% and 80.5% identity on the nucleotide and amino acid level, respectively (FIG. 8). The amplified 400 bp DNA fragment may be used to target a selectable marker gene to the K. lactis PMT1 chromosomal locus in analogy to the experiment described under E.6. leading to a disrupted gene. This will yield a K. lactis strain with reduced Ser/Thr specific mannosyltransferase activity. In addition, the amplified fragment may be used as homologous hybridization probe for the cloning of the entire K. lactis PMT1 gene using standard procedures.

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
  ( A ) LENGTH: 3375 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Saccharomyces cerevisiae ( i x ) FEATURE:
  ( A ) NAME/KEY: CDS
  ( B ) LOCATION: 532..2985
  ( D ) OTHER INFORMATION: /product="PMT1 gene"

( x i ) SEQUENCE DESCRIPTION: SEQ ID NO: 1:

```
GCTTGTCTCC  TGTTCATTCT  ACGCTTGTCA  TCCACACTGG  CACCGGCAGC  GGCGCTGCTC          60

TGTGAGCTGT  CTTTATCCAG  CAGGCTCAAA  TAGACTTGTT  CTGCCTCATA  TACTGTTTTT         120

CATTAACCAG  TCTCCTGGCC  TCTTCTAATT  TCGAACCTGG  CAGAGACATG  AAGTTCCTCG         180

TTATAGATTA  ATCACCAATT  GTCCTCTTTC  AGCGCTTCTG  TTAGTTGGCC  TTATTTAACG         240

GATCTTTGCT  TCAATTACGC  TTTCATCCAA  CATTGCCAC   CCTTGGAACC  AGAAGAGAAT         300

ATACATCATT  CGGGGTTGCC  CTGCCCATTT  ATATCGTATA  TTGTGATGAT  ATACCTTTTT         360

TTTTTTTTC   GCTGCGTTTT  TTTTCTCGAC  ACGTGTCGAA  GAAGAGTTTG  GCGTTTCTAA         420

GCAGATCTTG  ATTATTTCG   AGCAGCAAAA  CAAGACAAAC  AGGTGCATTG  TTAAAGCGAG         480

GTAGTATCAG  AAGAGCCTAT  CAAGAAACAG  CTAACAGCTA  CAAGCACGGT  C ATG TCG          537
                                                            Met Ser
                                                             1
```

| | | | | | | | | | | | | | | | | |
|---|---|---|---|---|---|---|---|---|---|---|---|---|---|---|---|---|
| GAA | GAG | AAA | ACG | TAC | AAA | CGT | GTA | GAG | CAG | GAT | GAT | CCC | GTG | CCC | GAA | 585 |
| Glu | Glu | Lys | Thr | Tyr | Lys | Arg | Val | Glu | Gln | Asp | Asp | Pro | Val | Pro | Glu | |
| | | 5 | | | | 10 | | | | | | 15 | | | | |
| CTG | GAT | ATC | AAG | CAG | GGC | CCC | GTA | AGA | CCC | TTT | ATT | GTT | ACC | GAT | CCG | 633 |
| Leu | Asp | Ile | Lys | Gln | Gly | Pro | Val | Arg | Pro | Phe | Ile | Val | Thr | Asp | Pro | |
| | 20 | | | | 25 | | | | | 30 | | | | | | |
| AGT | GCC | GAA | TTG | GCC | TCG | TTA | CGA | ACC | ATG | GTC | ACT | CTT | AAA | GAG | AAG | 681 |
| Ser | Ala | Glu | Leu | Ala | Ser | Leu | Arg | Thr | Met | Val | Thr | Leu | Lys | Glu | Lys | |
| 35 | | | | | 40 | | | | | 45 | | | | | 50 | |
| CTG | TTA | GTG | GCC | TGT | CTT | GCT | GTC | TTT | ACA | GCG | GTC | ATT | AGA | TTG | CAT | 729 |
| Leu | Leu | Val | Ala | Cys | Leu | Ala | Val | Phe | Thr | Ala | Val | Ile | Arg | Leu | His | |
| | | | | 55 | | | | | 60 | | | | | 65 | | |
| GGC | TTG | GCA | TGG | CCT | GAC | AGC | GTG | GTG | TTT | GAT | GAA | GTA | CAT | TTC | GGT | 777 |
| Gly | Leu | Ala | Trp | Pro | Asp | Ser | Val | Val | Phe | Asp | Glu | Val | His | Phe | Gly | |
| | | | 70 | | | | | 75 | | | | | 80 | | | |
| GGG | TTT | GCC | TCG | CAA | TAC | ATT | AGG | GGG | ACT | TAC | TTC | ATG | GAT | GTG | CAT | 825 |
| Gly | Phe | Ala | Ser | Gln | Tyr | Ile | Arg | Gly | Thr | Tyr | Phe | Met | Asp | Val | His | |
| | | 85 | | | | 90 | | | | | 95 | | | | | |
| CCT | CCT | CTT | GCA | AAG | ATG | TTG | TAT | GCT | GGT | GTG | GCA | TCG | CTT | GGT | GGG | 873 |
| Pro | Pro | Leu | Ala | Lys | Met | Leu | Tyr | Ala | Gly | Val | Ala | Ser | Leu | Gly | Gly | |
| | 100 | | | | 105 | | | | | 110 | | | | | | |
| TTC | CAG | GGT | GAT | TTT | GAC | TTC | GAA | AAT | ATT | GGT | GAC | AGC | TTT | CCA | TCT | 921 |
| Phe | Gln | Gly | Asp | Phe | Asp | Phe | Glu | Asn | Ile | Gly | Asp | Ser | Phe | Pro | Ser | |
| 115 | | | | | 120 | | | | | 125 | | | | | 130 | |
| ACG | ACG | CCA | TAC | GTG | TTG | ATG | AGA | TTT | TTC | TCT | GCT | TCT | TTG | GGG | GCT | 969 |
| Thr | Thr | Pro | Tyr | Val | Leu | Met | Arg | Phe | Phe | Ser | Ala | Ser | Leu | Gly | Ala | |
| | | | | 135 | | | | | 140 | | | | | 145 | | |
| CTT | ACT | GTT | ATT | TTG | ATG | TAC | ATG | ACT | TTA | CGT | TAT | TCT | GGT | GTT | CGT | 1017 |
| Leu | Thr | Val | Ile | Leu | Met | Tyr | Met | Thr | Leu | Arg | Tyr | Ser | Gly | Val | Arg | |
| | | | 150 | | | | | 155 | | | | | 160 | | | |
| ATG | TGG | GTT | GCT | TTG | ATG | AGC | GCT | ATC | TGC | TTT | GCC | GTT | GAA | AAC | TCG | 1065 |
| Met | Trp | Val | Ala | Leu | Met | Ser | Ala | Ile | Cys | Phe | Ala | Val | Glu | Asn | Ser | |
| | | | 165 | | | | | 170 | | | | | 175 | | | |
| TAC | GTC | ACT | ATT | TCT | CGT | TAC | ATT | CTG | TTG | GAC | GCC | CCA | TTG | ATG | TTT | 1113 |
| Tyr | Val | Thr | Ile | Ser | Arg | Tyr | Ile | Leu | Leu | Asp | Ala | Pro | Leu | Met | Phe | |
| 180 | | | | | 185 | | | | | 190 | | | | | | |
| TTC | ATT | GCA | GCT | GCA | GTC | TAC | TCT | TTC | AAG | AAA | TAC | GAA | ATG | TAC | CCT | 1161 |
| Phe | Ile | Ala | Ala | Ala | Val | Tyr | Ser | Phe | Lys | Lys | Tyr | Glu | Met | Tyr | Pro | |
| 195 | | | | | 200 | | | | | 205 | | | | | 210 | |
| GCC | AAC | TCG | CTC | AAT | GCT | TAC | AAG | TCC | TTG | CTT | GCT | ACT | GGT | ATT | GCT | 1209 |
| Ala | Asn | Ser | Leu | Asn | Ala | Tyr | Lys | Ser | Leu | Leu | Ala | Thr | Gly | Ile | Ala | |
| | | | | 215 | | | | | 220 | | | | | 225 | | |
| CTT | GGT | ATG | GCA | TCT | TCA | TCC | AAA | TGG | GTT | GGT | CTT | TTC | ACG | GTT | ACA | 1257 |
| Leu | Gly | Met | Ala | Ser | Ser | Ser | Lys | Trp | Val | Gly | Leu | Phe | Thr | Val | Thr | |
| | | | 230 | | | | | 235 | | | | | 240 | | | |
| TGG | GTG | GGT | CTT | TTA | TGT | ATC | TGG | AGA | CTA | TGG | TTC | ATG | ATT | GGG | GAT | 1305 |
| Trp | Val | Gly | Leu | Leu | Cys | Ile | Trp | Arg | Leu | Trp | Phe | Met | Ile | Gly | Asp | |
| | | | 245 | | | | | 250 | | | | | 255 | | | |
| TTG | ACT | AAG | TCT | TCC | AAG | TCC | ATC | TTC | AAA | GTA | GCA | TTT | GCC | AAA | TTG | 1353 |
| Leu | Thr | Lys | Ser | Ser | Lys | Ser | Ile | Phe | Lys | Val | Ala | Phe | Ala | Lys | Leu | |
| | 260 | | | | | 265 | | | | | 270 | | | | | |
| GCC | TTC | TTG | TTG | GGT | GTG | CCT | TTT | GCC | CTT | TAT | CTG | GTC | TTC | TTT | TAT | 1401 |
| Ala | Phe | Leu | Leu | Gly | Val | Pro | Phe | Ala | Leu | Tyr | Leu | Val | Phe | Phe | Tyr | |
| 275 | | | | | 280 | | | | | 285 | | | | | 290 | |
| ATC | CAC | TTC | CAA | TCA | TTA | ACT | TTG | GAC | GGG | GAT | GGC | GCA | AGC | TTC | TTT | 1449 |
| Ile | His | Phe | Gln | Ser | Leu | Thr | Leu | Asp | Gly | Asp | Gly | Ala | Ser | Phe | Phe | |
| | | | | 295 | | | | | 300 | | | | | 305 | | |
| TCG | CCT | GAA | TTT | AGA | TCT | ACA | CTA | AAG | AAC | AAT | AAG | ATC | CCC | CAA | AAT | 1497 |
| Ser | Pro | Glu | Phe | Arg | Ser | Thr | Leu | Lys | Asn | Asn | Lys | Ile | Pro | Gln | Asn | |
| | | | 310 | | | | | 315 | | | | | 320 | | | |

```
GTC GTT GCT GAT GTC GGC ATT GGC TCC ATT ATC AGC TTG CGT CAT CTC   1545
Val Val Ala Asp Val Gly Ile Gly Ser Ile Ile Ser Leu Arg His Leu
            325             330             335

TCT ACC ATG GGC GGT TAT TTG CAT TCT CAT TCA CAC AAT TAT CCA GCT   1593
Ser Thr Met Gly Gly Tyr Leu His Ser His Ser His Asn Tyr Pro Ala
    340             345             350

GGT TCG GAA CAA CAA CAA AGC ACT TTA TAT CCT CAC ATG GAT GCC AAT   1641
Gly Ser Glu Gln Gln Gln Ser Thr Leu Tyr Pro His Met Asp Ala Asn
355             360             365             370

AAC GAT TGG TTG TTG GAA CTT TAC AAC GCA CCC GGC GAA TCT TTA ACA   1689
Asn Asp Trp Leu Leu Glu Leu Tyr Asn Ala Pro Gly Glu Ser Leu Thr
            375             380             385

ACA TTC CAA AAC CTA ACC GAT GGT ACC AAG GTC AGA CTA TTC CAC ACT   1737
Thr Phe Gln Asn Leu Thr Asp Gly Thr Lys Val Arg Leu Phe His Thr
    390             395             400

GTT ACA AGA TGT AGA TTA CAC TCT CAT GAC CAT AAG CCA CCC GTT TCA   1785
Val Thr Arg Cys Arg Leu His Ser His Asp His Lys Pro Pro Val Ser
405             410             415

GAA AGC AGC GAC TGG CAG AAG GAG GTT TCT TGT TAT GGT TAC AGC GGA   1833
Glu Ser Ser Asp Trp Gln Lys Glu Val Ser Cys Tyr Gly Tyr Ser Gly
    420             425             430

TTC GAC GGT GAT GCT AAT GAT GAC TGG GTT GTT GAG ATT GAT AAA AAG   1881
Phe Asp Gly Asp Ala Asn Asp Asp Trp Val Val Glu Ile Asp Lys Lys
435             440             445             450

AAT TCT GCT CCT GGA GTT GCC CAA GAA CGG GTC ATA GCT TTG GAC ACA   1929
Asn Ser Ala Pro Gly Val Ala Gln Glu Arg Val Ile Ala Leu Asp Thr
            455             460             465

AAG TTT AGA TTG AGA CAT GCT ATG ACA GGC TGT TAT TTG TTT TCC CAC   1977
Lys Phe Arg Leu Arg His Ala Met Thr Gly Cys Tyr Leu Phe Ser His
    470             475             480

GAA GTC AAG TTG CCA GCT TGG GGG TTC GAA CAA CAA GAA GTT ACC TGT   2025
Glu Val Lys Leu Pro Ala Trp Gly Phe Glu Gln Gln Glu Val Thr Cys
485             490             495

GCC TCC TCC GGT AGA CAT GAT TTA ACA TTG TGG TAC GTT GAG AAC AAC   2073
Ala Ser Ser Gly Arg His Asp Leu Thr Leu Trp Tyr Val Glu Asn Asn
    500             505             510

AGT AAC CCA TTG TTA CCA GAA GAT ACC AAG CGT ATT TCC TAT AAA CCT   2121
Ser Asn Pro Leu Leu Pro Glu Asp Thr Lys Arg Ile Ser Tyr Lys Pro
515             520             525             530

GCA AGC TTC ATT TCT AAA TTT ATT GAA TCC CAT AAA AAG ATG TGG CAT   2169
Ala Ser Phe Ile Ser Lys Phe Ile Glu Ser His Lys Lys Met Trp His
            535             540             545

ATC AAT AAA AAT TTG GTC GAA CCT CAT GTT TAT GAA TCA CAA CCA ACT   2217
Ile Asn Lys Asn Leu Val Glu Pro His Val Tyr Glu Ser Gln Pro Thr
    550             555             560

TCA TGG CCA TTC TTG CTA CGT GGT ATA AGT TAC TGG GGT GAA AAT AAC   2265
Ser Trp Pro Phe Leu Leu Arg Gly Ile Ser Tyr Trp Gly Glu Asn Asn
565             570             575

AGA AAC GTC TAT CTA TTA GGT AAT GCG ATC GTA TGG TGG GCT GTC ACC   2313
Arg Asn Val Tyr Leu Leu Gly Asn Ala Ile Val Trp Trp Ala Val Thr
    580             585             590

GCT TTC ATC GGT ATT TTC GGA TTG ATT GTT ATC ACT GAG CTG TTC TCG   2361
Ala Phe Ile Gly Ile Phe Gly Leu Ile Val Ile Thr Glu Leu Phe Ser
595             600             605             610

TGG CAG TTA GGT AAA CCA ATT TTG AAG GAC TCC AAG GTT GTT AAC TTC   2409
Trp Gln Leu Gly Lys Pro Ile Leu Lys Asp Ser Lys Val Val Asn Phe
            615             620             625

CAC GTT CAG GTT ATT CAC TAC TTA TTG GGT TTT GCC GTC CAT TAT GCT   2457
His Val Gln Val Ile His Tyr Leu Leu Gly Phe Ala Val His Tyr Ala
    630             635             640
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CCA | TCT | TTC | TTA | ATG | CAA | CGT | CAA | ATG | TTT | TTG | CAT | CAC | TAC | TTA | CCT | 2505 |
| Pro | Ser | Phe | Leu | Met | Gln | Arg | Gln | Met | Phe | Leu | His | His | Tyr | Leu | Pro |      |
|     | 645 |     |     |     | 650 |     |     |     |     | 655 |     |     |     |     |     |      |
| GCT | TAT | TAT | TTC | GGT | ATT | CTT | GCC | CTT | GGC | CAC | GCC | TTG | GAC | ATA | ATA | 2553 |
| Ala | Tyr | Tyr | Phe | Gly | Ile | Leu | Ala | Leu | Gly | His | Ala | Leu | Asp | Ile | Ile |      |
|     | 660 |     |     |     | 665 |     |     |     |     | 670 |     |     |     |     |     |      |
| GTT | TCT | TAT | GTT | TTC | CGC | AGC | AAG | AGA | CAA | ATG | GGC | TAC | GCG | GTA | GTG | 2601 |
| Val | Ser | Tyr | Val | Phe | Arg | Ser | Lys | Arg | Gln | Met | Gly | Tyr | Ala | Val | Val |      |
| 675 |     |     |     |     | 680 |     |     |     |     | 685 |     |     |     |     | 690 |      |
| ATC | ACT | TTC | CTT | GCT | GCT | TCT | GTG | TAT | TTC | TTC | AAG | AGC | TTC | AGT | CCA | 2649 |
| Ile | Thr | Phe | Leu | Ala | Ala | Ser | Val | Tyr | Phe | Phe | Lys | Ser | Phe | Ser | Pro |      |
|     |     |     |     | 695 |     |     |     |     | 700 |     |     |     |     | 705 |     |      |
| ATT | ATT | TAC | GGT | ACA | CCA | TGG | ACT | CAA | GAA | TTG | TGT | CAA | AAA | TCG | CAG | 2697 |
| Ile | Ile | Tyr | Gly | Thr | Pro | Trp | Thr | Gln | Glu | Leu | Cys | Gln | Lys | Ser | Gln |      |
|     |     |     | 710 |     |     |     | 715 |     |     |     |     | 720 |     |     |     |      |
| TGG | TTG | TCT | GGT | TGG | GAC | TAC | AAT | TGT | AAC | ACA | TAC | TTT | TCT | TCA | TTA | 2745 |
| Trp | Leu | Ser | Gly | Trp | Asp | Tyr | Asn | Cys | Asn | Thr | Tyr | Phe | Ser | Ser | Leu |      |
|     |     | 725 |     |     |     |     | 730 |     |     |     |     | 735 |     |     |     |      |
| GAA | GAG | TAC | AAA | AAC | CAA | ACC | TTG | ACT | AAA | CGT | GAA | TCT | CAA | CCT | GCC | 2793 |
| Glu | Glu | Tyr | Lys | Asn | Gln | Thr | Leu | Thr | Lys | Arg | Glu | Ser | Gln | Pro | Ala |      |
|     | 740 |     |     |     |     | 745 |     |     |     |     | 750 |     |     |     |     |      |
| GCC | ACT | AGT | ACA | GTT | GAA | GAA | ATC | ACT | ATA | GAA | GGG | GAC | GGT | CCG | TCG | 2841 |
| Ala | Thr | Ser | Thr | Val | Glu | Glu | Ile | Thr | Ile | Glu | Gly | Asp | Gly | Pro | Ser |      |
| 755 |     |     |     |     | 760 |     |     |     |     | 765 |     |     |     |     | 770 |      |
| TAT | GAA | GAT | CTC | ATG | AAC | GAG | GAT | GGC | AAG | AAA | ATC | TTT | AAA | GAC | ACA | 2889 |
| Tyr | Glu | Asp | Leu | Met | Asn | Glu | Asp | Gly | Lys | Lys | Ile | Phe | Lys | Asp | Thr |      |
|     |     |     |     | 775 |     |     |     |     | 780 |     |     |     |     | 785 |     |      |
| GAA | GGT | AAT | GAA | CTA | GAT | CCA | GAA | GTT | GTC | AAA | AAA | ATG | TTG | GAA | GAG | 2937 |
| Glu | Gly | Asn | Glu | Leu | Asp | Pro | Glu | Val | Val | Lys | Lys | Met | Leu | Glu | Glu |      |
|     |     |     | 790 |     |     |     | 795 |     |     |     |     | 800 |     |     |     |      |
| GAG | GGA | GCT | AAC | ATT | TTA | AAA | GTA | GAA | AAA | AGG | GCT | GTT | TTG | GAA | TAAATTTC | 2992 |
| Glu | Gly | Ala | Asn | Ile | Leu | Lys | Val | Glu | Lys | Arg | Ala | Val | Leu | Glu |     |      |
|     |     | 805 |     |     |     |     | 810 |     |     |     |     | 815 |     |     |     |      |

|                                                                            |      |
|----------------------------------------------------------------------------|------|
| AGTACTCTCC ACATTTTTAT GTAAAGTCTT CTATAAGCTC TCGAGCGTAT AATTAAAAAC           | 3052 |
| GAAAATAGAC AAAAAAAACA TCATGAATAA AAAAAATGTC TTGAAGCTGA CTATATTGTC           | 3112 |
| CATCTGCGTT TAGAGACACG TATTCTATTT CGCTCAAATA AGTATGATCT GCAAGTAGTT           | 3172 |
| TCAGTGGTAT TATCATTTCG CACCGTTTTT TTTCCAAGAA CTCGTTTACG TGCCGCGAAA           | 3232 |
| AGTCTATCGA ATAGGCATTC GAGAACAATA GAAAGGAAC AGAAGCGTAG TACATATTAT            | 3292 |
| GCATAGACCC GTTTCTTTTC TTCTTTTTCG AAAATATTCT TATTGATTTA ACAATTAAGC           | 3352 |
| AGGTGTGTAA GATCAGAACT GCA                                                  | 3375 |

( 2 ) INFORMATION FOR SEQ ID NO: 2:

( i ) SEQUENCE CHARACTERISTICS:
        ( A ) LENGTH: 817 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| Met | Ser | Glu | Glu | Lys | Thr | Tyr | Lys | Arg | Val | Glu | Gln | Asp | Asp | Pro | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Glu | Leu | Asp | Ile | Lys | Gln | Gly | Pro | Val | Arg | Pro | Phe | Ile | Val | Thr |
|     |     |     | 20  |     |     |     |     | 25  |     |     |     |     | 30  |     |     |
| Asp | Pro | Ser | Ala | Glu | Leu | Ala | Ser | Leu | Arg | Thr | Met | Val | Thr | Leu | Lys |
|     |     | 35  |     |     |     |     | 40  |     |     |     |     | 45  |     |     |     |
| Glu | Lys | Leu | Leu | Val | Ala | Cys | Leu | Ala | Val | Phe | Thr | Ala | Val | Ile | Arg |

-continued

|   |   |   |   | 50 |   |   |   |   | 55 |   |   |   |   | 60 |   |
|---|---|---|---|---|---|---|---|---|---|---|---|---|---|---|---|
| Leu | His | Gly | Leu | Ala | Trp | Pro | Asp | Ser | Val | Val | Phe | Asp | Glu | Val | His |
| 65 |   |   |   | 70 |   |   |   |   | 75 |   |   |   |   |   | 80 |
| Phe | Gly | Gly | Phe | Ala | Ser | Gln | Tyr | Ile | Arg | Gly | Thr | Tyr | Phe | Met | Asp |
|   |   |   |   | 85 |   |   |   |   | 90 |   |   |   |   | 95 |   |
| Val | His | Pro | Pro | Leu | Ala | Lys | Met | Leu | Tyr | Ala | Gly | Val | Ala | Ser | Leu |
|   |   |   | 100 |   |   |   |   | 105 |   |   |   |   | 110 |   |   |
| Gly | Gly | Phe | Gln | Gly | Asp | Phe | Asp | Phe | Glu | Asn | Ile | Gly | Asp | Ser | Phe |
|   |   | 115 |   |   |   |   | 120 |   |   |   |   | 125 |   |   |   |
| Pro | Ser | Thr | Thr | Pro | Tyr | Val | Leu | Met | Arg | Phe | Phe | Ser | Ala | Ser | Leu |
|   | 130 |   |   |   |   | 135 |   |   |   |   | 140 |   |   |   |   |
| Gly | Ala | Leu | Thr | Val | Ile | Leu | Met | Tyr | Met | Thr | Leu | Arg | Tyr | Ser | Gly |
| 145 |   |   |   |   | 150 |   |   |   |   | 155 |   |   |   |   | 160 |
| Val | Arg | Met | Trp | Val | Ala | Leu | Met | Ser | Ala | Ile | Cys | Phe | Ala | Val | Glu |
|   |   |   |   | 165 |   |   |   |   | 170 |   |   |   |   | 175 |   |
| Asn | Ser | Tyr | Val | Thr | Ile | Ser | Arg | Tyr | Ile | Leu | Leu | Asp | Ala | Pro | Leu |
|   |   |   | 180 |   |   |   |   | 185 |   |   |   |   | 190 |   |   |
| Met | Phe | Phe | Ile | Ala | Ala | Ala | Val | Tyr | Ser | Phe | Lys | Lys | Tyr | Glu | Met |
|   |   | 195 |   |   |   |   | 200 |   |   |   |   | 205 |   |   |   |
| Tyr | Pro | Ala | Asn | Ser | Leu | Asn | Ala | Tyr | Lys | Ser | Leu | Leu | Ala | Thr | Gly |
|   | 210 |   |   |   |   | 215 |   |   |   |   | 220 |   |   |   |   |
| Ile | Ala | Leu | Gly | Met | Ala | Ser | Ser | Ser | Lys | Trp | Val | Gly | Leu | Phe | Thr |
| 225 |   |   |   |   | 230 |   |   |   |   | 235 |   |   |   |   | 240 |
| Val | Thr | Trp | Val | Gly | Leu | Leu | Cys | Ile | Trp | Arg | Leu | Trp | Phe | Met | Ile |
|   |   |   |   | 245 |   |   |   |   | 250 |   |   |   |   | 255 |   |
| Gly | Asp | Leu | Thr | Lys | Ser | Ser | Lys | Ser | Ile | Phe | Lys | Val | Ala | Phe | Ala |
|   |   |   | 260 |   |   |   |   | 265 |   |   |   |   | 270 |   |   |
| Lys | Leu | Ala | Phe | Leu | Leu | Gly | Val | Pro | Phe | Ala | Leu | Tyr | Leu | Val | Phe |
|   |   | 275 |   |   |   |   | 280 |   |   |   |   | 285 |   |   |   |
| Phe | Tyr | Ile | His | Phe | Gln | Ser | Leu | Thr | Leu | Asp | Gly | Asp | Gly | Ala | Ser |
|   | 290 |   |   |   |   | 295 |   |   |   |   | 300 |   |   |   |   |
| Phe | Phe | Ser | Pro | Glu | Phe | Arg | Ser | Thr | Leu | Lys | Asn | Asn | Lys | Ile | Pro |
| 305 |   |   |   |   | 310 |   |   |   |   | 315 |   |   |   |   | 320 |
| Gln | Asn | Val | Val | Ala | Asp | Val | Gly | Ile | Gly | Ser | Ile | Ile | Ser | Leu | Arg |
|   |   |   |   | 325 |   |   |   |   | 330 |   |   |   |   | 335 |   |
| His | Leu | Ser | Thr | Met | Gly | Gly | Tyr | Leu | His | Ser | His | Ser | His | Asn | Tyr |
|   |   |   | 340 |   |   |   |   | 345 |   |   |   |   | 350 |   |   |
| Pro | Ala | Gly | Ser | Glu | Gln | Gln | Gln | Ser | Thr | Leu | Tyr | Pro | His | Met | Asp |
|   |   | 355 |   |   |   |   | 360 |   |   |   |   | 365 |   |   |   |
| Ala | Asn | Asn | Asp | Trp | Leu | Leu | Glu | Leu | Tyr | Asn | Ala | Pro | Gly | Glu | Ser |
|   | 370 |   |   |   |   | 375 |   |   |   |   | 380 |   |   |   |   |
| Leu | Thr | Thr | Phe | Gln | Asn | Leu | Thr | Asp | Gly | Thr | Lys | Val | Arg | Leu | Phe |
| 385 |   |   |   |   | 390 |   |   |   |   | 395 |   |   |   |   | 400 |
| His | Thr | Val | Thr | Arg | Cys | Arg | Leu | His | Ser | His | Asp | His | Lys | Pro | Pro |
|   |   |   |   | 405 |   |   |   |   | 410 |   |   |   |   | 415 |   |
| Val | Ser | Glu | Ser | Ser | Asp | Trp | Gln | Lys | Glu | Val | Ser | Cys | Tyr | Gly | Tyr |
|   |   |   | 420 |   |   |   |   | 425 |   |   |   |   | 430 |   |   |
| Ser | Gly | Phe | Asp | Gly | Asp | Ala | Asn | Asp | Asp | Trp | Val | Val | Glu | Ile | Asp |
|   |   | 435 |   |   |   |   | 440 |   |   |   |   | 445 |   |   |   |
| Lys | Lys | Asn | Ser | Ala | Pro | Gly | Val | Ala | Gln | Glu | Arg | Val | Ile | Ala | Leu |
|   | 450 |   |   |   |   | 455 |   |   |   |   | 460 |   |   |   |   |
| Asp | Thr | Lys | Phe | Arg | Leu | Arg | His | Ala | Met | Thr | Gly | Cys | Tyr | Leu | Phe |
| 465 |   |   |   |   | 470 |   |   |   |   | 475 |   |   |   |   | 480 |

| | | | | | | | | | | | | | | |
|---|---|---|---|---|---|---|---|---|---|---|---|---|---|---|
| Ser | His | Glu | Val | Lys<br>485 | Leu | Pro | Ala | Trp<br>490 | Gly | Phe | Glu | Gln | Gln<br>495 | Glu | Val |
| Thr | Cys | Ala | Ser<br>500 | Ser | Gly | Arg | His<br>505 | Asp | Leu | Thr | Leu<br>510 | Trp | Tyr | Val | Glu |
| Asn | Asn | Ser<br>515 | Asn | Pro | Leu | Leu<br>520 | Pro | Glu | Asp | Thr | Lys<br>525 | Arg | Ile | Ser | Tyr |
| Lys | Pro<br>530 | Ala | Ser | Phe | Ile<br>535 | Ser | Lys | Phe | Ile | Glu<br>540 | Ser | His | Lys | Lys | Met |
| Trp<br>545 | His | Ile | Asn | Lys | Asn<br>550 | Leu | Val | Glu | Pro | His<br>555 | Val | Tyr | Glu | Ser | Gln<br>560 |
| Pro | Thr | Ser | Trp | Pro<br>565 | Phe | Leu | Leu | Arg | Gly<br>570 | Ile | Ser | Tyr | Trp | Gly<br>575 | Glu |
| Asn | Asn | Arg | Asn<br>580 | Val | Tyr | Leu | Leu | Gly<br>585 | Asn | Ala | Ile | Val | Trp<br>590 | Trp | Ala |
| Val | Thr | Ala<br>595 | Phe | Ile | Gly | Ile | Phe<br>600 | Gly | Leu | Ile | Val | Ile<br>605 | Thr | Glu | Leu |
| Phe | Ser<br>610 | Trp | Gln | Leu | Gly | Lys<br>615 | Pro | Ile | Leu | Lys | Asp<br>620 | Ser | Lys | Val | Val |
| Asn<br>625 | Phe | His | Val | Gln | Val<br>630 | Ile | His | Tyr | Leu | Leu<br>635 | Gly | Phe | Ala | Val | His<br>640 |
| Tyr | Ala | Pro | Ser | Phe<br>645 | Leu | Met | Gln | Arg | Gln<br>650 | Met | Phe | Leu | His | His<br>655 | Tyr |
| Leu | Pro | Ala | Tyr<br>660 | Tyr | Phe | Gly | Ile | Leu<br>665 | Ala | Leu | Gly | His<br>670 | Ala | Leu | Asp |
| Ile | Ile | Val<br>675 | Ser | Tyr | Val | Phe | Arg<br>680 | Ser | Lys | Arg | Gln | Met<br>685 | Gly | Tyr | Ala |
| Val | Val<br>690 | Ile | Thr | Phe | Leu | Ala<br>695 | Ala | Ser | Val | Tyr | Phe<br>700 | Phe | Lys | Ser | Phe |
| Ser<br>705 | Pro | Ile | Ile | Tyr | Gly<br>710 | Thr | Pro | Trp | Thr | Gln<br>715 | Glu | Leu | Cys | Gln | Lys<br>720 |
| Ser | Gln | Trp | Leu | Ser<br>725 | Gly | Trp | Asp | Tyr | Asn<br>730 | Cys | Asn | Thr | Tyr | Phe<br>735 | Ser |
| Ser | Leu | Glu | Glu<br>740 | Tyr | Lys | Asn | Gln | Thr<br>745 | Leu | Thr | Lys | Arg | Glu<br>750 | Ser | Gln |
| Pro | Ala | Ala<br>755 | Thr | Ser | Thr | Val | Glu<br>760 | Glu | Ile | Thr | Ile | Glu<br>765 | Gly | Asp | Gly |
| Pro | Ser | Tyr<br>770 | Glu | Asp | Leu | Met | Asn<br>775 | Glu | Asp | Gly | Lys<br>780 | Lys | Ile | Phe | Lys |
| Asp<br>785 | Thr | Glu | Gly | Asn | Glu<br>790 | Leu | Asp | Pro | Glu | Val<br>795 | Val | Lys | Lys | Met | Leu<br>800 |
| Glu | Glu | Glu | Gly | Ala<br>805 | Asn | Ile | Leu | Lys | Val<br>810 | Glu | Lys | Arg | Ala | Val<br>815 | Leu |
| Glu | | | | | | | | | | | | | | | |

( 2 ) INFORMATION FOR SEQ ID NO: 3:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO (vi) ORIGINAL SOURCE:
    (A) ORGANISM: Kluyveromyces lactis (ix) FEATURE:
    (D) OTHER INFORMATION: /product="part of PMT1 gene"

(xi) SEQUENCE DESCRIPTION: SEQ ID NO: 3:

TCTGCTCCTG GCGNAGCTCA AGTATNCGTT AAGGCTTTGG ACACTAAATT CAGATTGAGA    60

CATGCTATGA CTGGTTGTAG TATCTCACAT GAAGTCAAAT TACCAAAATG GGGCTTCGAA    120

CAACAG    126

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ATGGA Y GCNA A Y AA Y GA Y-
TG G    21

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GA Y GCNAA Y G A Y GA Y TGGGT    20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

TC Y TG Y TG Y T CRAANCCCCA    20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

CTRTTRTT Y T CNCCCCARTA    20

We claim:
1. Genetically engineered fungal cells carrying genetic modification(s) located in either (a) one or more coding regions or (b) one or more regions responsible for or involved in the expression and/or the transcriptional regulation, of one or more genes whose expression products are enzymes involved in the transfer of mannosyl residues from the Dol-P-Man donor to the hydroxyl group of one or more serine or threonine amino acids in a protein and causing said cells to have at least reduced capacity of O-glycosylation.

2. Fungal cell according to claim 1, wherein said modification(s) comprise any suppression, substitution, deletion, addition, disruption and/or mutational insertion.

3. Fungal cell according to claim 2, wherein said modification(s) are stable during segregation and/or non-reverting and/or non-leaky.

4. Fungal cell according to claim 1, wherein the reduced capacity of O-glycosylation results from the production of inactive enzymes, from the production of enzymes having altered biological properties, from the absence of production of said enzymes, or from the production of said enzymes at low levels.

5. Fungal cell according to claim 1, wherein said gene is the gene encoding the Dol-P-Man:Protein (Ser/Thr) Mannosyl Transferase whose sequence is represented in SEQ ID NO: 1.

6. Fungal cell according to claim 1 in which an exogenous DNA sequence has been introduced.

7. Fungal cell according to claim 6, wherein the exogenous DNA sequence comprises one or more genes encoding a desired protein to be expressed and/or secreted in said cell.

8. Fungal cell according to claim 7, wherein said DNA sequence is included in an expression cassette comprising a transcription and translation initiation region joined to the 5' end of said DNA sequence encoding the desired protein(s).

9. Fungal cell according to claim 8, wherein said transcription and translation initiation region is chosen from promoters derived from fungal cell genes.

10. Fungal cell according to claim 8, wherein said expression cassette further comprises a transcription and translation termination region at the 3' end of the DNA sequence encoding the desired protein(s).

11. Fungal cell according to claim 8, wherein said expression cassette further comprises a signal peptide (pre-sequence) at the N-terminus of the desired protein sequence so as to direct the nascent protein to the secretory pathway of said fungal cell.

12. Fungal cell according to any of claims 6 to 11, wherein the exogenous DNA sequence is part of a vector which may either replicate autonomously in said fungal cell or integrate into a fungal chromosome.

13. Fungal cell according to claim 1 chosen from the group consisting of filamentous fungi and yeast cells.

14. Fungal cell according to claim 13, wherein the filamentous fungi is chosen from the group consisting of Aspergillus, Trichoderma, Mucor, Neurospora, Fusarium.

15. Fungal cell according to claim 13, wherein the yeast is chosen from the group consisting of Kluyveromyces, Saccharomyces, Pichia, Hansenula, Candida, Schizosaccharomyces.

16. Fungal cell according to claim 15, wherein the yeast is chosen from the group consisting of Kluyveromyces, Saccharomyces, Pichia, Hansenula and Candida.

17. Process for the production of recombinant products, wherein a fungal cell according to claim 6 is cultivated in conditions in which the exogenous DNA sequence is expressed, and the product is recovered.

18. Process according to claim 17, wherein said product is secreted into the culture medium.

19. Process according to claim 17 or 18, wherein said product is susceptible to O-glycosylation by the fungal cell.

20. An isolated DNA molecule comprising a gene encoding the Dol-P-Man:Protein (Ser/Thr) Mannosyl Transferase of a Saccharomyces species, said gene having the sequence given in SEQ ID NO: 1.

21. An isolated DNA molecule comprising a gene encoding the Dol-P-Man:Protein (Ser/Thr) Mannosyl Transferase of a Kluyveromyces species, said gene containing the sequence given in SEQ ID NO: 3.

22. An isolated gene encoding a protein exhibiting properties of the Dol-P-Man:Protein (Ser/Thr) Mannosyl Transferase and comprising DNA sequences which hybridize at 42° C. in the presence of 5% formamide to one or both of primers Sq3908 SEQ ID NO: 4 and Sq3909 SEQ ID NO: 5 and one or both of primers Sq3910 SEQ ID NO: 6 and Sq3911 SEQ ID NO: 7.

* * * * *

UNITED STATES PATENT AND TRADEMARK OFFICE
CERTIFICATE OF CORRECTION

PATENT NO. : 5,714,377
DATED : February 3, 1998
INVENTOR(S) : Tanner et al.

It is certified that error appears in the above-identified patent and that said Letters Patent is hereby corrected as shown below:

On the title page item [56],
Pg. 1, Col. 3, line 42: After "...N-Glycosylation of", insert --Type I and--.

Pg. 2, Col. 2, line 14: After "...produced in", delete "chinese", and insert --Chinese--.

Col. 9, line 56: After "...0.9M", delete "NaCl90", and insert --NaCl, 90--.

Col. 13, line 35: After "...Mat", delete "a/αura3-52", and insert --a/α, ura3-52--.

Col. 24, line 31: After "...GAA", delete "TAAATTTC", and insert --TAAATTTCCC--.

Signed and Sealed this

Seventeenth Day of October, 2000

*Attest:*

Q. TODD DICKINSON

*Attesting Officer*        *Director of Patents and Trademarks*